(12) United States Patent
Hetting

(10) Patent No.: US 11,213,630 B2
(45) Date of Patent: Jan. 4, 2022

(54) INJECTOR FOR PREVENTING ACCIDENTAL NEEDLE STICKS

(71) Applicant: TINA HETTING HOLDING APS, Charlottenlund (DK)

(72) Inventor: Mikael Hetting, Charlottenlund (DK)

(73) Assignee: INJECTO GROUP A/S, Hellerup (DK)

( * ) Notice: Subject to any disclaimer, the term of this patent is extended or adjusted under 35 U.S.C. 154(b) by 841 days.

(21) Appl. No.: 15/579,327

(22) PCT Filed: Jun. 3, 2016

(86) PCT No.: PCT/DK2016/050164
§ 371 (c)(1),
(2) Date: Dec. 4, 2017

(87) PCT Pub. No.: WO2016/192739
PCT Pub. Date: Dec. 8, 2016

(65) Prior Publication Data
US 2018/0353706 A1 Dec. 13, 2018

(30) Foreign Application Priority Data

Jun. 3, 2015 (DK) .............................. PA201500324
Aug. 6, 2015 (DK) .............................. PA201500445

(51) Int. Cl.
*A61M 5/32* (2006.01)
*A61M 5/31* (2006.01)
(52) U.S. Cl.
CPC ........ *A61M 5/3213* (2013.01); *A61M 5/3137* (2013.01); *A61M 5/326* (2013.01); *A61M 5/3243* (2013.01); *A61M 5/3257* (2013.01)
(58) Field of Classification Search
CPC .............. A61M 5/3213; A61M 5/3137; A61M 5/3243; A61M 5/326
See application file for complete search history.

(56) References Cited

U.S. PATENT DOCUMENTS 2,860,635 A 11/1958 Wilburn
4,445,895 A * 5/1984 Margulies ............... A61M 5/24
604/193

(Continued)

FOREIGN PATENT DOCUMENTS

CN 2094999 U 2/1992
CN 201263820 Y 7/2009

(Continued)

OTHER PUBLICATIONS

PCT International Search Report for PCT International Patent Application No. PCT/DK2016/050164, dated Nov. 29, 2016.

*Primary Examiner* — Lauren P Farrar
(74) *Attorney, Agent, or Firm* — Holland & Hart LLP

(57) ABSTRACT

The present invention relates to an injector for preventing accidental needle sticks comprising:—a cylinder extending along a longitudinal axis, an inner wall and an outer wall, the cylinder having an outlet at an outlet end opposite an actuating end and a finger grip on the outer wall, which finger grip is positioned between the outlet end and the actuating end,—a piston having a piston body and a deformable sealing element, which deformable sealing element abuts the inner wall of the cylinder at an abutting interface and seals an annular gap between the piston body and the inner wall of the cylinder when the piston is inserted in the cylinder,—a needle guard for mounting on the outside of the cylinder from the outlet end or the actuating end, which needle guard comprises a barrel with a mounting end opposite an operating end, the barrel having a slot for receiving the finger grip of the cylinder when the needle guard is mounted on the cylinder, which slot extends from the mounting end towards the operating end, wherein when the needle guard is mounted on the cylinder from the actuating end in a protective position, the barrel extends along the longitudinal axis and projects beyond the outlet (Continued)

end of the cylinder so that when a hypodermic needle is attached at the outlet end, the barrel protects a user from accidental needle sticks.

14 Claims, 20 Drawing Sheets

(56) References Cited

U.S. PATENT DOCUMENTS

| | | | |
|---|---|---|---|
| 4,840,619 A | 6/1989 | Hughes | |
| 5,232,457 A | 8/1993 | Grim | |
| 5,364,369 A * | 11/1994 | Reynolds | A61J 1/2089 604/187 |
| 5,417,660 A | 5/1995 | Martin | |
| 5,713,871 A * | 2/1998 | Stock | A61M 5/3257 604/192 |
| 6,511,460 B1 * | 1/2003 | Arnissolle | A61M 5/3257 604/110 |
| 2005/0228345 A1 | 10/2005 | Yang et al. | |
| 2012/0116319 A1 * | 5/2012 | Grunhut | A61M 5/20 604/198 |
| 2012/0238966 A1 | 9/2012 | Kuracina | |
| 2013/0245561 A1 * | 9/2013 | Kouyoumjian | A61M 5/3294 604/191 |
| 2015/0051578 A1 | 2/2015 | Herr | |

FOREIGN PATENT DOCUMENTS

| | | |
|---|---|---|
| EP | 2752211 A1 | 7/2014 |
| WO | 1991001152 A1 | 2/1991 |
| WO | 0160435 A1 | 8/2001 |
| WO | 2005105184 A1 | 11/2005 |
| WO | 2014194918 A1 | 12/2014 |

* cited by examiner

INJECTOR FOR PREVENTING ACCIDENTAL NEEDLE STICKS

TECHNICAL FIELD

The present invention relates to injector for preventing accidental needle sticks. The injector comprises a needle guard, which needle guard when activated safeguards the needle by preventing access of a user to the hypodermic needle and mechanically locking the needle guard to the barrel of the injection device. The needle guard has dual function design where it functions firstly as extended plunger in cooperation with the needle cap to perform the injection and secondly as a needle guard safeguarding the needle and protecting the surroundings against needle stick injuries. The dual function steps are performed with the same hand wise configuration and hence without any change of finger grip or handling between the steps.

BACKGROUND

The problem of protection against needle stick injuries is well recognised but a sufficient solution has not been provided. Thus, there exists a variety of solutions and products that aim to solve the serious problem where hospital staff, especially doctors and nurses are often exposed to and suffer sharp injuries with used needles and syringes, which in many cases lead to the transfer of contagious and even deadly diseases.

The needle stick injuries most often occur because the user after a completed injection tries to secure the needle by way of the traditional needle cap which is detached before the injection, which procedure leads needle stick injuries by infected needles.

In addition, needle stick injuries can occur as a result of other situations, but regardless of the reason, the importance of reducing these injuries is crucial since on a daily basis people die due to needle stick injuries since having been infected with deadly diseases such as HIV and Hepatitis.

One of the key barriers to implementation and use of needle stick preventions, is that these often cost more than the customer is willing to pay or do not offer the ease of use required by the user. The high price of needle stick preventions is due to the fact that these are generally significantly more expensive to produce due to the extra components, raw materials and workflows which means significantly higher production price and thus also asking price. Besides the price which is the first prerequisite for a successful product implementation particularly user friendliness is of the utmost importance since injections which are given in millions on a daily basis worldwide are characterised by habit and conservatism, making the user likely to reject new solutions which often influence user friendliness negatively compared to the usual injection devices which have been used for decades.

Most needle stick preventions act as accessories which are usually attached to the standard needles which are mounted on disposable syringes, but these needle stick preventions require an additional workflow by the user after the injection, since the safeguarding of the needle must be made by manual positioning of the needle stick prevention over the needle tip, which is also connected with a relatively high risk of a needle stick injury, since this manoeuvre is difficult to implement with the injecting hand alone, and often requires the help of the non-injecting hand, which often results in needle stick injuries. With regard to user friendliness and not least safety it is notoriously essential that the needle be safeguarded by the injecting hand, since a large number of needle stick injuries occur when users must use their other hand to secure the needle or are uncertain of how to handle the actual product. For the same reason the World Health Organization (WHO) has prohibited other than the use of the injecting hand like recapping is forbidden as well (attaching the needle cap after injection).

There also exists disposable syringes which are designed with an integrated needle stick prevention but these solutions are often complicated both in terms of a large number of additional components and significantly increased production costs while at the same time significantly reducing safety and ease of use and especially the price is prohibitive for implementation of those in large volumes, since the components among other things, increase the physical size of the syringe significantly.

The latter type syringes are typically provided with a protective piece for enclosing of the needle, but there are also syringes which retract the needle into the barrel by the end of the injection. However, it is very important to point out that the latter type syringes can function appropriately only if the user conducts the injection according to instructions and thus leads the plunger to the bottom of the barrel which is a necessity to activate the mechanism that secures the needle in the barrel. Otherwise, the syringe can be used a large number of times if the user has a demand and deliberately keeps the piston a few millimetres from the bottom of the cylinder during injection.

It is the purpose of the present invention to solve the problems previously unsolved, and in particular to introduce a needle guard which is affordable, user friendly and integrated in a syringe. The invention is mainly dedicated to prefilled syringes although it can be utilised for other medical applications and purposes.

SUMMARY

The present invention relates to an injector for preventing accidental needle sticks comprising
  a cylinder extending along a longitudinal axis, an inner wall and an outer wall, the cylinder having an outlet at an outlet end opposite an actuating end and a finger grip on the outer wall, which finger grip is positioned between the outlet end and the actuating end,
  a piston having a piston body and a deformable sealing element, which deformable sealing element abuts the inner wall of the cylinder at an abutting interface and seals an annular gap between the piston body and the inner wall of the cylinder when the piston is inserted in the cylinder,
  a needle guard for mounting on the outside of the cylinder from the outlet end or the actuating end, which needle guard comprises a barrel with a mounting end opposite an operating end, the barrel having a slot for receiving the finger grip of the cylinder when the needle guard is mounted on the cylinder, which slot extends from the mounting end towards the operating end,
  wherein when the needle guard is mounted on the cylinder from the actuating end in a protective position, the barrel extends along the longitudinal axis and projects beyond the outlet end of the cylinder so that when a hypodermic needle is attached at the outlet end, the barrel protects a user from accidental needle sticks.

The invention thus presents modifications of the existing components in addition to a new component in the form of a needle guard, which in combination are able to achieve a unique technical solution and solve the serious problem of reducing needle stick injuries. No previously suggested device is capable of safeguarding the needle tip by continuation of the empty sequence with unchanged finger grip which meets the WHO's desire to ensure early activation reuse at the same time. According to the present invention the needle guard comprises a single additional component and has a unique design, for integration in an injection device.

The injector may be any kind of injector employed to deliver a pharmaceutical composition to a subject through the skin of the subject. For example, the injector may be a syringe, which is fitted with a hypodermic needle to inject a pharmaceutical composition, e.g. via subcutaneous (SC), intramuscular (IM), intra-dermal (ID), or intravenous (IV) delivery or another type of delivery.

The injector comprises a cylinder. In the context of the invention a "cylinder" is any kind of tube or the like allowing the piston to be moved from one position in the cylinder to another. The cylinder has an "actuating end" and "outlet end" opposite each other. The actuating end of the cylinder allows access to the piston for moving it, i.e. "actuating" the piston, in the cylinder. Likewise, the piston may have an actuating surface facing the actuating end of the cylinder and an outlet surface opposite the actuating surface thus facing the outlet end of the cylinder. In general, the distance from the actuating end of the cylinder to the outlet end of the cylinder minus the dimension of the piston parallel with the longitudinal axis of the cylinder defines an "operating length" of the cylinder. The piston may be moved towards the outlet end using any means from the actuating end, for example the piston may be moved towards the outlet end using a piston rod or a plunger. It is preferred that the piston cannot be moved towards the actuating end, e.g. from the outlet end, with engagement of the piston, e.g. with a piston rod or the like, from the actuating end.

The cylinder comprises a finger grip positioned between the outlet end and the actuating end. The finger grip may have any form desired, which allows the user to rest one or more fingers, e.g. two finger, while using a further finger to push the needle guard. For example, the finger grip may contain two protrusion or the like on the outer wall of the cylinder. In another embodiment the cylinder has a single finger grip which is fitted with a ring or the like surrounding the cylinder thereby allowing the user to rest two fingers on the ring.

The cylinder can be considered to define a guarding length from the finger grip to the tip of a hypodermic needle, when the hypodermic needle is attached to the cylinder at the outlet end, wherein the longitudinal dimension of the slot for receiving the finger grip is equal to or larger than the guarding length, and the length of the barrel is equal to or larger than a total length of the cylinder from the actuating end of the cylinder to the tip of a hypodermic needle, when the hypodermic needle is attached to the cylinder at the outlet end. The slot for receiving the finger grip of the cylinder may have any shape desirable, for example it may be straight or curved, e.g. having a helical shape. The cylinder may be made from any relevant material, and typical materials comprise polymeric materials, such as cyclic olefin copolymer (COC), e.g. TOPAS polymers (supplied by TOPAS Advanced Polymers GmbH), cyclo olefin polymer (COP), or polystyrene, or glasses. COC polymers are preferred due to their excellent barrier characteristics and thus accommodate the need for long-term storage of pharmaceutical agents. It is also contemplated that the cylinder may be made from a metal or it may comprise any combination of polymeric materials, glasses or metals. The cross-sectional shape of the cylinder is not limited although it is preferred that the cylinder has a round cross-section. It is also contemplated that the cross-section may be oval, elliptical, polygonal, etc. When the cylinder has a round cross-section the diameter, e.g. the inner diameter, may have any value conventionally used with syringes. For example, in a preferred embodiment the cylinder has an inner diameter in the range of about 2 mm to about 10 mm, such as 4.65 mm, 6.35 mm or 8.80 mm.

The cylinder at the actuating may be open across the whole cross-section of the cylinder, which allows removal and insertion of the piston and thereby also filling of the injector via the actuating end. The cylinder may also have at the actuating end a ridge or protrusion(s) or the like preventing removal of the piston once inserted in the cylinder. In particular, the ridge or protrusion(s) may provide a "lock device" of a "spring-lock device" where the complementary "spring device" is contained on a piston rod. A spring-lock device or the like can lock the piston rod after moving the piston to the outlet end of the cylinder thereby preventing refilling of the cylinder.

The injector comprises a piston, which seals the contents of the cylinder from the surroundings. The piston has a piston body and a deformable sealing element, which deformable sealing element abuts the inner wall of the cylinder at an abutting interface and seals an annular gap between the piston and the inner wall of the cylinder. The term "abutting interface" refers to any section where the inner wall and the deformable sealing elements contact each other and the "abutting interface" does not impose any limitations on either the inner wall of the cylinder or the surface of the sealing element. The piston will thus define an outlet section of the cylinder, i.e. at the outlet surface of the piston, of the piston, and an actuation section of the cylinder, i.e. at the actuating surface of the piston, and prevent fluid communication from the outlet section to the actuation section, or vice versa, past the piston. Movement of the piston in the cylinder towards the outlet end will thereby eject fluid present in the outlet section e.g. via an outlet. The piston body does not abut the inner wall of the cylinder, and only sealing elements present on the piston body abut the inner wall of the cylinder. The piston may have one or more deformable sealing elements.

The injector has a needle guard comprising a barrel. The barrel has a slot for receiving the finger grip of the cylinder; the slot extends from the mounting end towards the operating end so that the needle guard can be mounted on the cylinder from the outlet end or the actuating end. When the needle guard is mounted from the outlet end, i.e. with the finger grip in the slot for receiving the finger grip, the barrel shields the user of the injector from a needle attached to the outlet of cylinder before the injector is used. This position is generally referred to as a storage position. When the needle guard is mounted on the cylinder from the actuating end with the finger grip in the slot for receiving the finger grip the needle guard has a protective position after injection of a patient where the barrel extends along the longitudinal axis and projects beyond the outlet end of the cylinder so that when a hypodermic needle is attached at the outlet end, the barrel protects a user from accidental needle sticks. In an embodiment of the invention a hypodermic needle is attached, e.g. permanently attached, to the outlet of the cylinder.

The needle guard achieves the safeguarding of the needle simply by continuation of the injection action and hence without any change of finger grip or hand configuration. This effect is achieved by introducing the slots in the barrel which allow for the passage of the barrel of the finger grip which according to the invention and in contrast to usual syringe barrels is positioned further down the cylinder and away from the actuating end of the cylinder.

The injector for preventing accidental needle sticks of the invention thus has a storage position where the needle guard is mounted from the outlet end. In this position the needle guard will protect the user from contact with the hypodermic needle when handling the injector prior to injecting the contents of the cylinder into a patient (see e.g. FIG. 6 and FIG. 13). The injector is prepared for injecting the contents of the cylinder into a patient by removing the needle guard from its storage position and mounting the needle guard on the cylinder from the actuating end (see e.g. FIG. 7 and FIG. 14). The contents of the cylinder are administered to the patient by pushing the needle guard, with a device for actuating the piston provided in the needle guard or with an external plunger or the like, towards the outlet end of the cylinder; when the piston has reached the outlet end (see e.g. FIG. 8 and FIG. 15), and the needle guard is in a "post injection position", the hypodermic needle is withdrawn from the patient, and the pushing movement, e.g. of the user's thumb, is continued to move the needle guard to its protective position (see e.g. FIG. 9 and FIG. 16) where the user is prevented from touching the hypodermic needle so that he is protected from accidental needle sticks. In any embodiment of the invention the needle guard may be longer than the total length of the cylinder including a hypodermic needle attached to the cylinder (as illustrated in FIG. 4 and FIG. 5), which affords an additional level of protection for the user. Likewise, in any embodiment of the invention the needle guard may have the same length of the total length of the cylinder including a hypodermic needle attached to the cylinder (as illustrated in FIG. 9). This embodiment is considered to afford sufficient protection to the user.

The needle guard is preferably a single component, e.g. manufactured by injection moulding from a thermoplastic material although it can be made from glass or other material relevant for the purpose. Through its design the needle guard, in preferred embodiments where the needle guard is provided with a device for actuating the piston, achieves a dual functionality firstly as extended plunger in cooperation with the needle cap and secondly as needle guard for safeguarding of the needle. The injector may also have a separate plunger, which can engage the piston allowing the user to fill the injector before using the needle guard when injecting the contents of the injector into the patient so that the user is protected after the injection.

For reduced production costs utmost diligence has been present in order to design the needle guard for achieving the simplest moulding cycle and as such the needle guard according to the invention can be moulded in a standard mould despite the presence of protrusions and slots and at a significantly low cycle time per moulding sequence.

In an embodiment the needle guard is provided with a device for actuating the piston, which can move the piston from the actuating end towards the outlet end of the cylinder when the needle guard is mounted on the cylinder from the actuating end. The device for actuating the piston may be a rod, e.g. a plunger. When the needle guard comprises a device for actuating the piston the design of the needle guard enables the user to protect himself, in a simple manner, against undesired contact with the needle tip simply by continuing the emptying movement by use of one and same hand and unchanged finger grip until the barrel encloses the needle in which position the barrel may be locked. Furthermore, when the barrel of the injector is locked after emptying reuse of the injector is prevented, e.g. regardless whether the user chooses to use the needle cap to secure the needle or not.

The device for actuating the piston may be selected freely. In a specific embodiment the device for actuating the piston is a compression spring arranged at the operating end of the needle guard. The compression spring may for example be a helical compression spring. In an embodiment the compression spring has a compression constant, k, in the range of 0.01 N/mm to 1 N/mm, e.g. 0.05 N/mm to 0.5 N/m, as determined from the relation: $k=F/X$, where F is the force applied and X is the displacement of the compression spring. The spring may have a length in an uncompressed state in the range of 5 mm to 100 mm, e.g. 20 mm to 50 mm, but the length in the uncompressed state, and also the minimal length in the compressed state, will be chosen relative to the size of the injector. The compression spring may be an internal compression spring, which is compressed against the top surface of the piston by manual actuation of needle guard via a push plate and at a given application of force causes the piston to move towards the bottom of the cylinder whereby injection is executed. The force of the compression spring is calculated from the number of turns, spring wire diameter and the length and the result is dedicated the desire to transfer the force to the piston by compression of the spring so that the piston, when the given force is obtained, moves towards the cylinder outlet for execution of injection. In this embodiment it is preferred that a hypodermic needle is attached to the outlet of the cylinder. It is further preferred in this embodiment that the injector is prefilled.

With its flexibility and variable length depending on the force applied the compression spring ensures completion of the injection before the needle cap moves over the needle and subsequently the needle tip. In an embodiment permanent securing of the needle and thereby the user's safety is achieved by locking the barrel at the end of the barrel's movement which may be obtained by outward protrusions, e.g. in the form of barbs, of the barrel in cooperation with a backstop on the cylinder. In a preferred embodiment, the outward protrusions of the barrel are slanted and form a wedge-shaped profile in which the height of the protrusions increase in the direction against the closed end of the needle cap and are wedged in between the outer wall of the barrel and edge of the finger grip in order to create a backstop between the slanted outward protrusions perpendicular surface and the perpendicular surface edge of the finger grip. The mechanical backstop opposite the emptying direction is achieved when the slanted outward protrusions on their highest point have a height dimension which is greater than the recess but which due to the flexibility of the plastic component material and at the applied force are positioned through the opening which is created between the outer wall of the cylinder and the finger grip, and eventually wedged below and past the edge of the finger grip.

The use of a compression spring for starting movement of the piston and the execution of the full injection also represent significant user related advantages during the injection, since the initial movement of the piston always occurs at the same force application, irrespective of whether the spring is compressed quickly or slowly which adverse handling often occurs because users handle injection tools differently depending on physical differences between individuals. According to the invention the piston will commence movement at one particular application of force due to the force of the piston and friction relating to the surrounding cylinder inner wall, which will reduce undue discomfort which is frequently experienced by patients receiving injections and instead give each injection identical smooth and comfortable characteristics for both user and patient.

In another embodiment the device for actuating the piston is a needle cap having a tubular section with a fastening end comprising a device for fastening, e.g. releasably fastening, the needle cap to an inside wall of the barrel, which needle cap has a length, which is equal to or larger than an operating length of the cylinder defined by the distance from the actuating end of the cylinder to the outlet end of the cylinder minus the dimension of the piston parallel with the longitudinal axis. The needle cap is thus located inside the barrel so that when the needle guard is mounted in the storage position from the outlet end, i.e. with the finger grip in the slot for receiving the finger grip, the needle cap surrounds a hypodermic needle attached to the outlet of the cylinder. In this embodiment it is preferred that a hypodermic needle is attached to the outlet of the cylinder. It is further preferred in this embodiment that the injector is prefilled.

The needle cap may be rigid or made from an elastomeric material. In a specific embodiment the barrel is flexible in a transverse direction, and the needle cap at the fastening end has a fastening device for engaging a complementary fastening device on the inside wall of the barrel, which provide a device for releasably fastening the needle cap to the inside wall of the barrel. The barrel may have an oval transverse cross section, which provides flexibility. In this embodiment the smallest inner dimension is larger than, e.g. approximately equal to, the largest outer diameter of the cylinder leaving necessary room for expansion of the barrel. Thus, when the needle guard is mounted on the cylinder at the actuating end with the finger grip in the slot for receiving the finger grip the needle cap will push the piston towards the outlet end. When the barrel has an oval transverse cross section the inner wall of the barrel may, at its smallest inner transverse dimension, comprise two inner opposite outward protrusions interacting with the needle cap comprising a circular recess, each representing the respective fastening device and complementary fastening device. Upon continued application of force to the needle guard the piston, having reached the outlet end of the cylinder, i.e. the post-injection position, will stop the movement of the needle cap and further force a transverse expansion of the smallest dimension of the barrel so that the transverse flexibility of the barrel releases the fastening of the needle cap, which in turn allows the needle guard to be moved to its protective position.

In another aspect the invention relates to an injector comprising:
a cylinder with a longitudinal axis and an inner wall and an outlet at an outlet end of the cylinder opposite an actuating end of the cylinder,
a piston having a piston body and a deformable sealing element, which deformable sealing element abuts the inner wall of the cylinder at an abutting interface and seals an annular gap between the piston body and the inner wall of the cylinder when the piston is inserted in the cylinder,
a needle cap having a tubular section for actuating the piston, which needle cap has a needle insertion end comprising an engagement device for sealingly engaging a complementary engagement device of the outlet of the cylinder when the needle cap is mounted on the cylinder, which needle cap has a length, which is equal to or larger than an operating length of the cylinder defined by the distance from the actuating end of the cylinder to the outlet end of the cylinder minus the dimension of the piston parallel with the longitudinal axis, which tubular section consists of an elastomeric material. It is preferred that the injector comprises a hypodermic needle attached to the outlet of the cylinder. Any variation of the needle cap used in this aspect may be employed as needle cap in the first aspect of the invention.

The needle cap in this aspect can advantageously serve both as a cap for sealing the contents of the injector, due to the elastomeric nature of the tubular section, and also serve as a piston rod for actuating the piston. Thus, the elastomeric material will seal the hypodermic needle and prevent the contents of the syringe from leaking or evaporating. The elastomeric material will also prevent contaminants from entering into the cylinder and thus prevent the contamination of a pharmaceutical composition, e.g. a drug or a vaccine, in the cylinder. The piston may be solid so that its insertion in the cylinder is not dependent on its orientation. This simplifies the manufacturing of the injector compared to injectors having a piston rod engaging a piston with means for receiving the piston rod. Furthermore, since the sealing effect is provided from the material of the needle cap no additional features are needed in order to seal the injector, making this aspect especially advantageous for prefilled injectors. In a preferred embodiment the injector is prefilled. The removal of the need of additional features for sealing the injector emphasises the advantages obtained with a solid piston with respect to simplifying manufacture. However, in another embodiment the needle cap comprises a plug, which plug seals the hypodermic needle when the engagement device is engaging the complementary engagement device of the outlet of the cylinder.

Any elastomeric material may be used for the tubular section, but it is preferred that the elastomeric material is a thermoplastic elastomer (TPE). The TPE may for example be a styrene block copolymer (SBC) selected from the list consisting of hydrogenated SBC or non hydrogenated SBS or alloys of these. In particular the tubular section may have a Shore A hardness in the range of 50 to 90, e.g. in the range of 70 to 90. A Shore A hardness in the range of 50 to 90 allows that the needle cap consists of the elastomeric material, since a needle cap with this Shore A hardness is sufficiently rigid despite the elastic nature of the material for the needle cap to be employed as a piston rod. In particular, when a needle cap Shore A hardness in the range of 50 to 90 can be used to actuate the piston without a collapse of the material, so that the injector can be emptied. The wall thickness of the tubular section will typically be in the range of 0.5 mm to 5 mm. The needle cap can also comprise other materials, e.g. harder plastic material such as ABS material, poly ethylene (PE), poly propylene (PP) or vulcanized rubber material or other material relevant for the purpose. The needle cap may for example combine a rigid outer material such as ABS, PE, or PP with a softer inner material for embedding of the needle tip, said softer material having a Shore hardness of between 29 and 80, such as Evoprene G966 or Evoprene G967.

In an embodiment needle cap at a needle protection end opposite the needle insertion end has a push-plate having a larger transverse dimension than a transverse dimension of the needle cap. The push plate may be disc shaped. The push plate may further comprise an elastomeric material, e.g. the push plate may consist of an elastomeric material. The push plate may be used for pushing, e.g. with a finger, the piston towards the outlet end of the cylinder using the needle cap as a piston rod. The push-plate may have any size, e.g. with respect to the cross-sectional area, as deemed appropriate for the intended use. However, the push-plate typically has a larger cross-sectional area than the cross-sectional area of the cylinder. For example, the push-plate may be round and have a diameter of up to twice the inner diameter of the cylinder. The presence of a push-plate increases the stability during administration of the injection which is of great importance when exercising human injections. Furthermore, the push plate increases user comfort when operating the syringe, which is especially relevant during injections with larger syringes where the force needed to initiate movement of the piston (break loose force) is substantial compared to smaller syringes. Consequently, the push plate area is typically increased with increased cylinder diameter of which the latter is the governing parameter for the force needed to empty the cylinder. The push-plate may have any shape but it will typically be a disc or an annular ring.

In a specific embodiment the engagement device comprises a lower material thickness than the material thickness of the tubular section. For example the material thickness of the engagement device may in the range of 0.2 mm to 3.0 mm, e.g. 0.5 mm to 2.0 mm, depending on the cylinder nominal volume and ultimately the size of the cylinder. A lower material thickness is especially suited for injectors having a glass cylinder where the outlet of the cylinder is typically produced with higher measurement values and tolerances than can be afforded e.g. by injection moulding of thermoplastic materials. Therefore, the lower material thickness at the engagement device allows the needle cap to be used with injectors with glass cylinders. An injector with a glass cylinder will typically have a hypodermic needle attached to the outlet of the cylinder. The same effect can be obtained when the engagement device comprises perforations or an inner cross-sectional area of the engagement device is larger than an inner cross-sectional area of the tubular section. Thus, an engagement device comprising perforations is likewise suited for use with an injector having a glass cylinder, and as is an engagement device having an inner cross-sectional area of the engagement device larger than the inner cross-sectional area of the tubular section.

In a particular embodiment the needle cap comprises a push plate and the needle cap consists of the elastomeric material as defined above. This embodiment is particularly suited for use in the first aspect of the invention where the push plate of the needle cap forms the device for fastening, i.e. releasably fastening, the needle cap to an inside wall of the barrel, which is fitted with protrusions for engaging the push plate. The elastomeric nature of the push plate provides that the needle cap is releasably fastened to a complementary fastening device on the inside wall of the barrel. Thereby the fastening will be released when moving the needle guard, i.e. using the needle guard with the needle cap for actuating the piston, from the post-injection position to the protective position. A push plate of an elastomeric material is particularly suited for any design of the needle cap as used a device for actuating the piston.

The second aspect of the invention enables manufacturers of syringe cylinders to maintain their existing design and infra structure in production and instead of redesigning their cylinder in order to accommodate a needle cap which can be used as plunger or piston rod, the manufacturers can implement the needle cap of the invention which is highly affordable compared to redesigning the cylinder.

The material has an elasticity necessary to expand over a tubular outlet and maintain this position during a shelf life of up to at least three years and when removed from its position is capable of contracting to at least a size and diameter enabling its insertion in the cylinder.

The needle cap may comprise a closed end which may be of a certain thickness in order to embed the hypodermic needle in the needle cap material when the needle cap is mounted on the outlet of the cylinder. The needle cap has a design and a flexible material capable of expanding and contracting around an interacting component such as a tubular outlet of a cylinder for an injector containing a liquid medical substance, and where the $1^{st}$ expansion and contraction is achieved during mounting of the needle cap before use, and the $2^{nd}$ expansion and contraction is achieved when the needle cap is removed from its position over the outlet of the syringe cylinder inserted into the cylinder to function as a plunger.

In a further embodiment the needle cap comprises, at the tubular section for actuating the piston, an air plug device, e.g. with respect to the cylinder, which air plug device forms an airtight barrier between the air plug device and the inner wall of the cylinder when the needle cap is inserted into the cylinder. The air plug device is preferably located at the end opposite the needle insertion end. Thus, when the needle cap having an air plug device is inserted into the cylinder a volume of enclosed air will form in the cylinder between the surface of the piston and the air plug device, and when the needle cap is pushed towards the outlet end of the cylinder the enclosed air will be compressed so that the compressed air pushes the piston thereby ultimately moving the piston to the outlet end for injection execution by emptying the cylinder. The needle cap with an air plug device thus enables a reduced length of the needle cap. When the needle cap comprises an air plug device the needle cap is not required to have the length defined above but may be shorter. The needle cap, including the length of the air plug device, and the length of the compressed air must together be equal to, or larger than, the operating length of the cylinder. For example, the needle cap with an air plug device may have a length of 70% to 95% of the operating length. In general, this embodiment employs a clearance between the actuating end of the cylinder and the actuating surface of the piston, of e.g. 5 mm to 20 mm, allowing formation of the volume of compressed air. This embodiment is particularly relevant for injectors with cylinders with low inner diameters, and especially injectors of small volumes, e.g. about 1 ml or less. For example, the inner diameter of the cylinder may be 5 mm or less.

An injector having a needle cap with an air plug device is not limited to having a needle cap with a tubular section consisting of an elastomeric material as defined above, and in a third aspect the invention relates to an injector comprising:
  a cylinder with a longitudinal axis and an inner wall and an outlet at an outlet end of the cylinder opposite an actuating end of the cylinder,
  a piston having a piston body and a deformable sealing element, which deformable sealing element abuts the inner wall of the cylinder at an abutting interface and seals an annular gap between the piston body and the inner wall of the cylinder when the piston is inserted into the cylinder,
  a needle cap having a tubular section for actuating the piston, which needle cap has a needle insertion end comprising an engagement device for engaging a complementary engagement device of the outlet of the cylinder when the needle cap is mounted on the cylinder, which needle cap has a length, which is equal to or larger than an operating length of the cylinder defined by the distance from the actuating end of the cylinder to the outlet end of the cylinder minus the dimension of the piston parallel with the longitudinal axis, which needle cap at the tubular section for actuating the piston comprises an air plug device as defined above. The air plug device is preferably at the end opposite the needle insertion end. The material of the needle cap in this aspect may be chosen freely, and in a specific embodiment it is injection moulded from a thermoplastic polymer. However, all variations and embodiments of the needle cap described for the second aspect of the invention are also relevant for this aspect of the invention.

In either aspect of the injector the piston may be injection moulded from a TPE, in particular having a Shore A hardness in the range of 50 to 90. A piston having a Shore A hardness in the range of 50 to 90 allows that the piston is used without lubrication. In another embodiment the injector does not comprise a lubricant.

The injector may comprise, e.g. at the outlet end, a fitting for attaching or mounting a hypodermic needle. The cylinder may thus have a tapered outlet, e.g. a tubular outlet, from the cylinder providing an engagement device for engaging a complementary engagement device of a hypodermic needle, e.g. the engagement device and the complementary engagement device may comprise a male-female interaction, with the tubular outlet optionally comprising an external thread, e.g. a helical external thread, and the hypodermic needle optionally comprising a complementary internal thread, e.g. a helical internal thread. A hypodermic needle may be fitted to allow simple removal, and replacement, of the hypodermic needle, or the hypodermic needle may be mounted permanently on the injector. In particular, the hypodermic needle may be mounted on the injector so that its removal requires the destruction of the injector thereby preventing reuse, which in the context of the invention is considered "permanent".

In an embodiment of the invention the injector, preferably prefilled, is a syringe with a hypodermic needle. The syringe may have a hypodermic needle mounted, e.g. permanently mounted, on a tubular outlet or an outlet of another shape. When the injector is prefilled, in particular when it also comprises a needle cap for use as a piston rod, there may be a clearance between the actuating end of the cylinder and the actuating surface of the piston. The clearance ensures stability of a piston rod when this is inserted in the cylinder, which results in a safer and easier operation of the injector. The clearance, e.g. measured in units of length, may be any value relevant for the size, e.g. volume, of injector and the dose of pharmaceutical composition in the injector. Typical values for the clearance are between about 2 mm to about 20 mm.

In an embodiment the piston has two or more deformable sealing elements, and the piston is solid, i.e. it does not have a cavity or the like. A solid piston having two or more deformable sealing elements may be symmetrical relative to a transverse plane so that its orientation when inserted in the cylinder is not relevant. In contrast, an asymmetrical piston, e.g. a piston having a cavity, such as a cavity for housing a piston rod, needs to be oriented prior to insertion into the cylinder, e.g. so that the piston may be actuated by the needle cap inserted in the cavity. The removal of the need to orient the piston greatly simplifies production of syringes, e.g. prefilled syringes, and thereby reduces the production costs. It is preferred that the solid piston does not comprise any means to engage a piston rod or plunger. Similarly the replacement of a traditional needle cap by the needle cap of the invention reduces the production costs by eliminating a traditional plunger connected to the piston.

The piston comprises a deformable sealing element. In the context of the invention, the term "deformable" describes that the deformable sealing element may be deformed and thereby seal an annular gap between the piston and the inner wall of the cylinder. The deformable sealing element will thus have dimensions in a relaxed state, e.g. in a state without deformation, such as deformation caused by inserting the piston in a cylinder, and the diameter, e.g. of the piston including the deformable sealing element, in the relaxed state will be larger than the inner diameter of the cylinder of the injector. This ensures that the deformable sealing element will seal the annular gap between the piston and the inner wall of the cylinder. The diameter of the deformable sealing element is typically 3% to 20% larger than the inner diameter of the cylinder, e.g. 5% to 15% larger.

At the location where the deformable sealing element abuts the inner wall of the cylinder the interface between the deformable sealing element and the inner wall will provide a static friction and a dynamic friction. Movement of the piston in the cylinder will require application of a force sufficient to overcome initially the static friction and subsequently the dynamic friction; the static friction will be larger than the dynamic friction and thereby the force to provide an initial movement of the piston is larger than the force required to provide a sustained movement of the piston. Once the piston has stopped moving the force to provide an initial movement must be overcome again. In general, the inner wall of the cylinder requires lubrication in order to keep the dynamic friction sufficiently low to ensure sufficient glide for the piston and allow for easy movement of the piston in the cylinder and thereby easy delivery of a pharmaceutical composition during injection. In a specific embodiment the injector, e.g. the piston, does not comprise a lubricant; in particular when the deformable sealing element has a Shore A hardness in the range of 50 to 90, e.g. 70 to 80, no lubricant is needed.

The piston may be made from any material. In particular, the piston body is not in contact with the inner wall of the cylinder and the material of the piston body is generally only required to be inert with respect to any pharmaceutical composition in the injector. The deformable sealing element should likewise be inert with respect to the pharmaceutical composition in the injector. In a certain embodiment of the invention the piston and the deformable sealing element are of the same material, e.g. the piston body and the deformable sealing element are of the same material. By providing the piston, e.g. the piston body, and the deformable sealing element, and any optional supporting sealing elements, from the same material, a more cost-effective and simple production is made possible, thereby to a large extend avoiding different process steps e.g. time-consuming assembly.

The deformable sealing element is made from a material of an appropriate hardness and elasticity to ensure that the annular gap between the piston and the inner wall of the cylinder is sealed. Any such material may be chosen for the deformable sealing element. In a preferred embodiment the piston of the invention is made by injection moulding from an appropriate TPE. Any TPE may be used. Appropriate thermoplastic polymers comprise styrene block copolymers (SBCs), e.g. hydrogenated—H-SBC—(SEBS—styreneethylene butylenes-styrene or similar) or non hydrogenated (SBS—styrene-butadienestyrene) or alloys of these and other compatible polymers. Preferred SBCs are those known under the trademark Evoprene as marketed by AlphaGary Corporation (Leominster, Mass., USA). Evoprenes are described in the brochure "EVOPRENE™ Thermoplastic Elastomer (TPE) Compounds—GENERAL INFORMATION" (published by AlphaGary, July 2007), and preferred Evoprene™ polymers are Evoprene™ Super G, Evoprene™ G, Evoprene™ GC, and Evoprene™ HP, which are described in the brochures "EVOPRENE™ SUPER G Thermoplastic Elastomer (TPE) Compounds", "EVOPRENE™ G Thermoplastic Elastomer (TPE) Compounds", "EVOPRENE™ GC Thermoplastic Elastomer (TPE) Compounds", and EVOPRENE™ HP Thermoplastic Elastomer (TPE) Compounds (published by AlphaGary, July 2007), respectively. The contents of all mentioned brochures by AlphaGary are hereby incorporated by reference. When the piston is injection moulded the piston can be made with lower tolerances that afforded by technologies such as vulcanisation, which is commonly used in the manufacture of traditional rubber pistons. Appropriate materials comprise elastomers, such as rubbers, e.g. natural rubber, synthetic rubber (polyisoprene rubber, butyl rubber), silicone rubber, and the like, which may be defined with respect to e.g. the Shore durometer, which indicates the elasticity of the elastomeric material and measures the hardness of the elastomeric material, where the higher the durometer, the harder the compound. For example, in an embodiment of the invention the deformable sealing element has or the piston and the deformable sealing element have a Shore A hardness in the range of about 50 to about 90, preferably 60 to 80, more preferred 71 to 76. The terms "Shore hardness" and "Shore durometer" may be used interchangeably. In general, the deformable sealing element will be homogeneous and composed of the same material throughout the volume of the deformable sealing element, which material has a Shore A hardness in the given ranges. By using a material with a Shore A hardness in the above mentioned range, a relatively hard elastomeric material is provided. It should be noted that Shore A durometer is only one of many ways to characterise the material properties of the chosen material, and that other tests may also be employed to characterise the material.

The surface of the deformable sealing element may have any shape desired. In a certain embodiment the deformable sealing element has a convex surface, although the surface is not limited to convex shapes. In this context the term "convex" means that a straight line between any two points within the deformable sealing element does not cross the surface of the deformable sealing element.

The cylinder and/or the barrel may each be one single component preferably made from injection moulded plastic material known as COC or COP with characteristics similar to glass and with excellent barrier characteristics although it can be made of other plastic material or glass or any other material relevant for the purpose. The barrel design is unusual since the finger grips are positioned downstream of the barrel towards the needle, which is necessary for optimum interaction with the needle guard during safeguarding of the needle. The interaction of the barrel with the needle guard for safeguarding of the needle is achieved through the interaction between the needle guard's slots and the barrel's finger grips whereas the slots allow for the necessary travel distance of the needle guard in order to pass and ultimately safeguard the needle. The relationship between the slots and the position of the finger grip(s) is unusual compared to regular syringes with incorporated means of needle stick protection, due to the absence of slots and traditional position of the barrel's finger grips by the open end of the barrel. The position of the finger grip of the barrel is calculated with respect to the length and width of the slot in such a way that the finger grips are not positioned further away from the needle than the length between finger grip upper edge and needle tip plus the addition of a comfortable safety margin to ensure full and sufficient safeguarding of the needle. The barrel may further be equipped with guide vanes in the area of the barrels open end ensuring correct horizontal mounting of the needle guard before injection leading to correct interaction between the slots and the finger grips.

The invention may function in the following way. Prior to injection the needle guard may be mechanically linked to the needle cap via the interaction between inner outward protrusions of the barrel and the e.g. circular activating end of the device for actuating the piston which two interacting components are dismantled from their needle protective and sealing position at the barrel's needle end and mounted in the barrel with the needle cap's open end first according to the barrel's orientation guide vanes ensuring the correct positioning of the slots of the needle guard with respect to passing the barrel's finger grips, where after the injection is executed by activation of the needle guard's operating end towards the needle by which the needle cap's open end abuts and forces the piston downward through the cylinder until the piston reaches and stops at the time of completed injection. After withdrawing the injector from the injection area and without change of finger grip or hand attitude safeguarding of the needle is obtained by continued application of force via downward activation of the needle guard which forces the barrel past the tip of the hypodermic needle attached to the outlet of the cylinder, e.g. by forcing lower outward protrusions' slanted surfaces against the upper surface of the barrel causing a sideways movement of the needle guard which may expands due to an oval shape allowing for further expansion due to the flexible oval expanding perpendicularly and over its shortest diameter and allowing the protrusions departure from their surrounding of the needle cap's fastening end to continue their motion towards passing and enclosing the tip of the hypodermic needle, which is achieved with a minimum safety margin preventing inadvertent contact with the hypodermic needle at the same time as the lower outward protrusions of the cylinder pass and interlock against the barrel's inward protrusions establishing a strong mechanical back stop and ultimately a safeguarding of the hypodermic needle.

In an embodiment the barrel of the needle guard is flexible in its transverse direction in order to achieve firstly the outward protrusions' departure from surrounding of the circular fastening end of the needle cap and secondly in order to achieve the outward protrusions' passing of and interlocking against the barrel's inward protrusions, which flexibility can be achieved either by choosing a flexible material or achieved as described in the preferred embodiment of the invention where the barrel is oval-shaped allowing the temporary expansion of the needle guard at its smallest diameter. The combination of material and shape decides which final shape barrel of the needle guard will have according to the wanted functionality. Although the preferred needle guard embodiment has an oval-shaped barrel the barrel can be circular, square shaped or have any shape as long as the material is flexible enough to accommodate the necessary expansion needed. The inner protrusions of the barrel may be rectangular, circular, quadratic or square shaped although a triangular shape has been chosen to illustrate the lower outward protrusions in needle guards longitudinal axis with the hypotenuse pointing down and inward and the upper outward protrusions being parallel to the opposite slanted surface of the barrel's inward protrusion with which the needle guard's outward protrusion interacts during interlocking between the needle guard and the barrel.

The area between the upper and lower protrusion of the needle guard may be round, square, rectangular or have any shape suitable for mechanical interaction with the needle cap's activating end's shape. The needle cap's fastening end interacting can be with right angles to its vertical plane, it can be square, rounded or any shape as long as it can mechanically interact with the area between the needle guard's upper and lower protrusions. In an alternative embodiment of the invention the needle guard comprises two oppositely positioned protrusions for mechanical interaction with a circular recess, e.g. a push plate, of a needle cap's fastening end which recess accommodates the protrusions. The needle cap's recess can be circular, quadratic, rectangular, or square shaped. Similarly the areas surrounding the recess may have rounded or angled characteristics.

The barrel's outward protrusions may be circular, quadratic, rectangular, or square shaped although a triangular.

BRIEF DESCRIPTION OF THE DRAWINGS

In the following the invention will be explained in greater detail with the aid of an example and with reference to the schematic drawings, in which.

DETAILED DESCRIPTION

The present invention relates to injector for preventing accidental needle sticks and to an injector. The present invention will now be described in greater detail with reference to the appended drawings. The figures are generally depicted as "cross-sectional views" of the injectors of the invention, where certain figures present side views where the injector in the "cross-sectional view" is depicted at an angle of 90° compared to the injector otherwise depicted.

Figure 1:
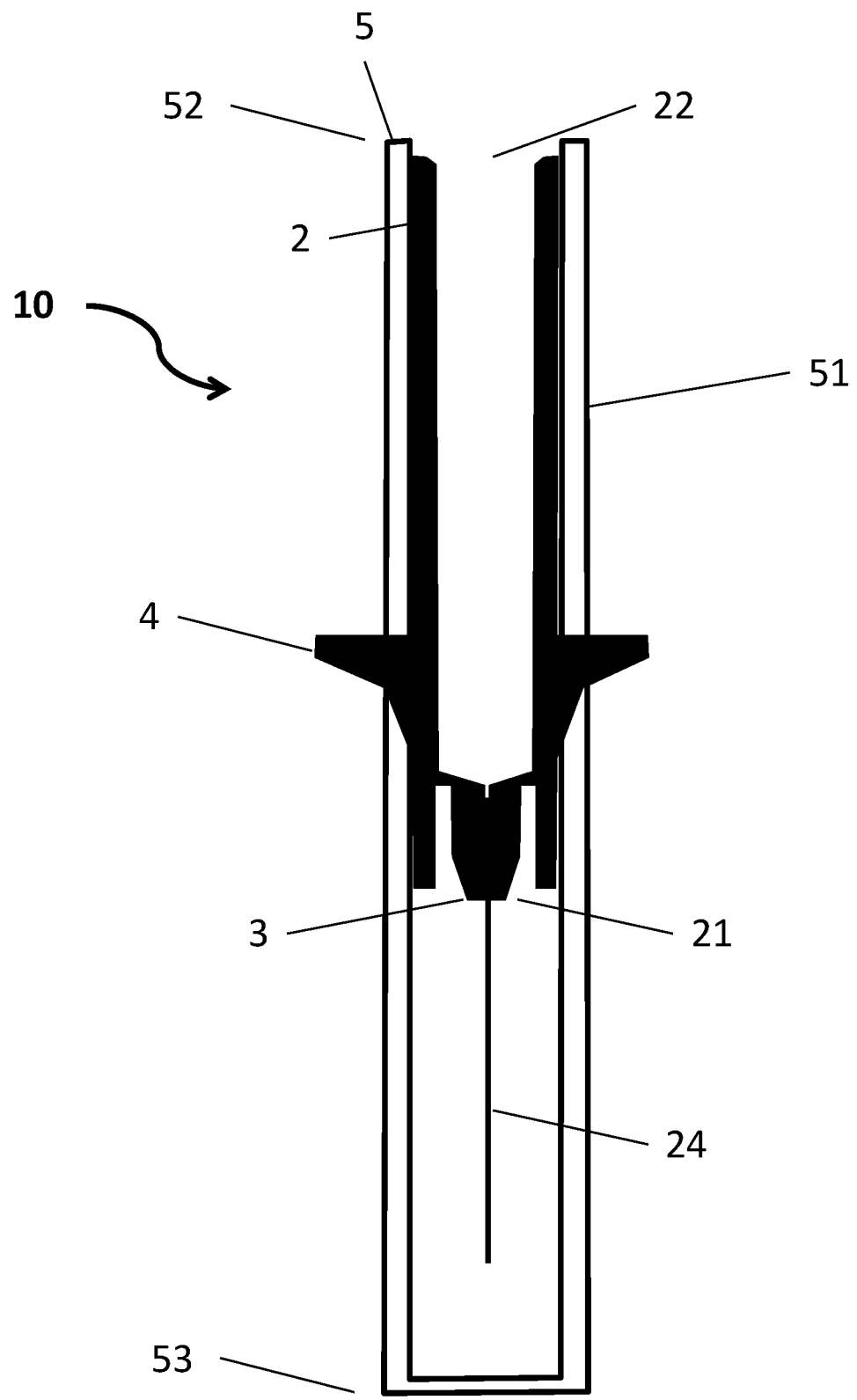
FIG. 1 shows an embodiment of an injector for preventing accidental needle sticks of the invention in a storage position.
Figure 2:
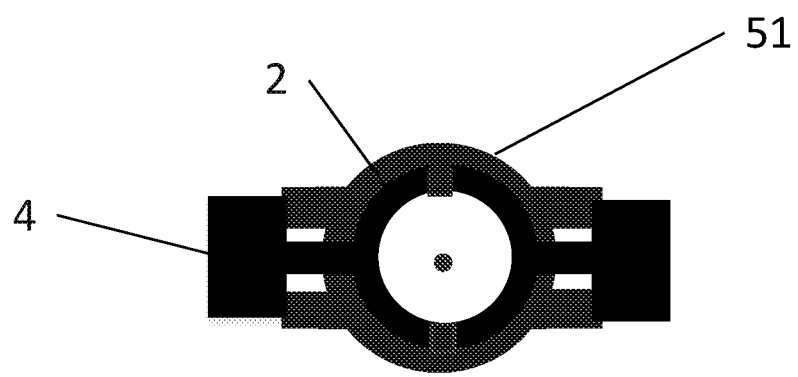
FIG. 2 shows a top view of an injector for preventing accidental needle sticks of the invention.
Figure 3:
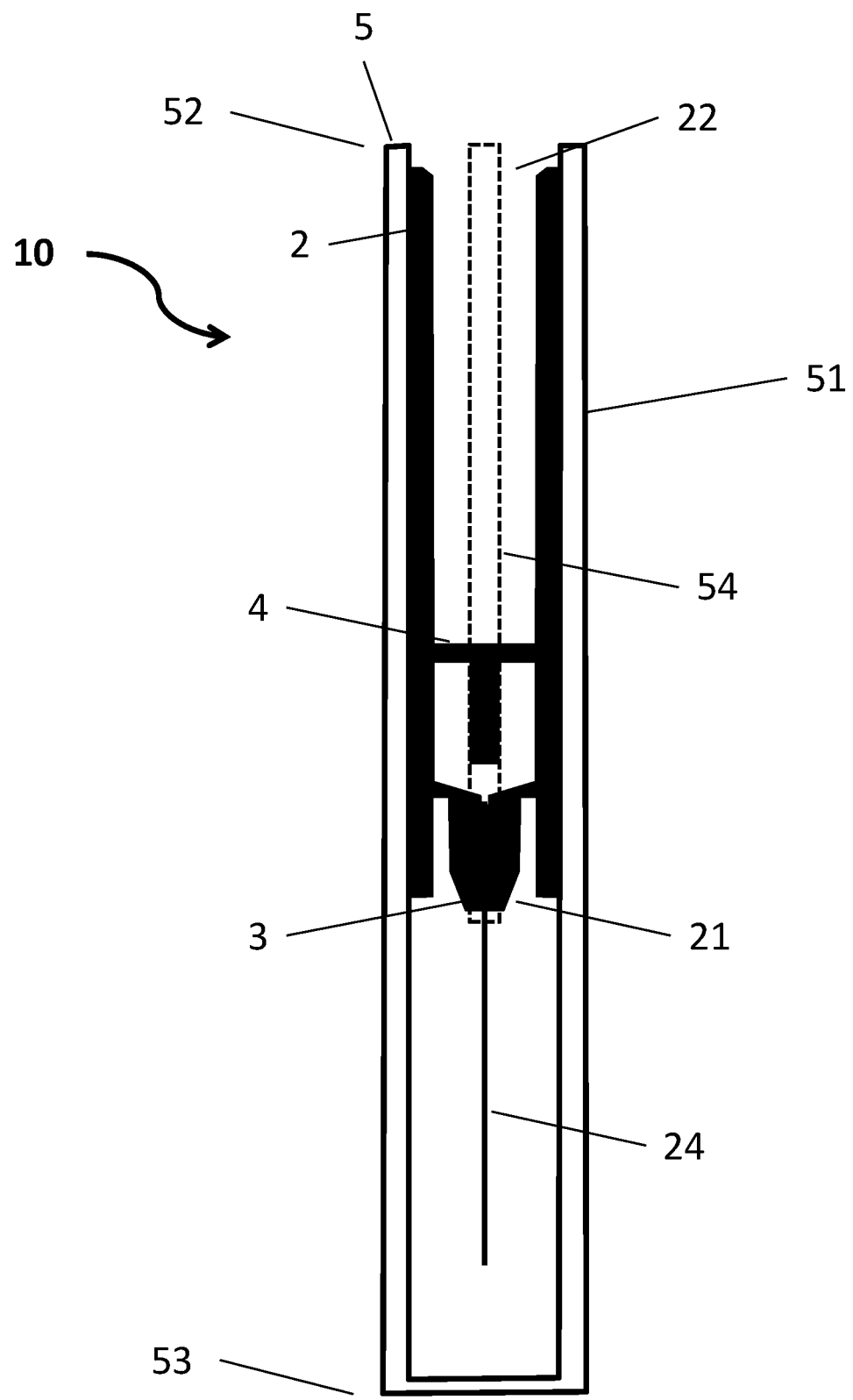
FIG. 3 shows a side view of an injector for preventing accidental needle sticks of the invention in a storage position.
Figure 4:
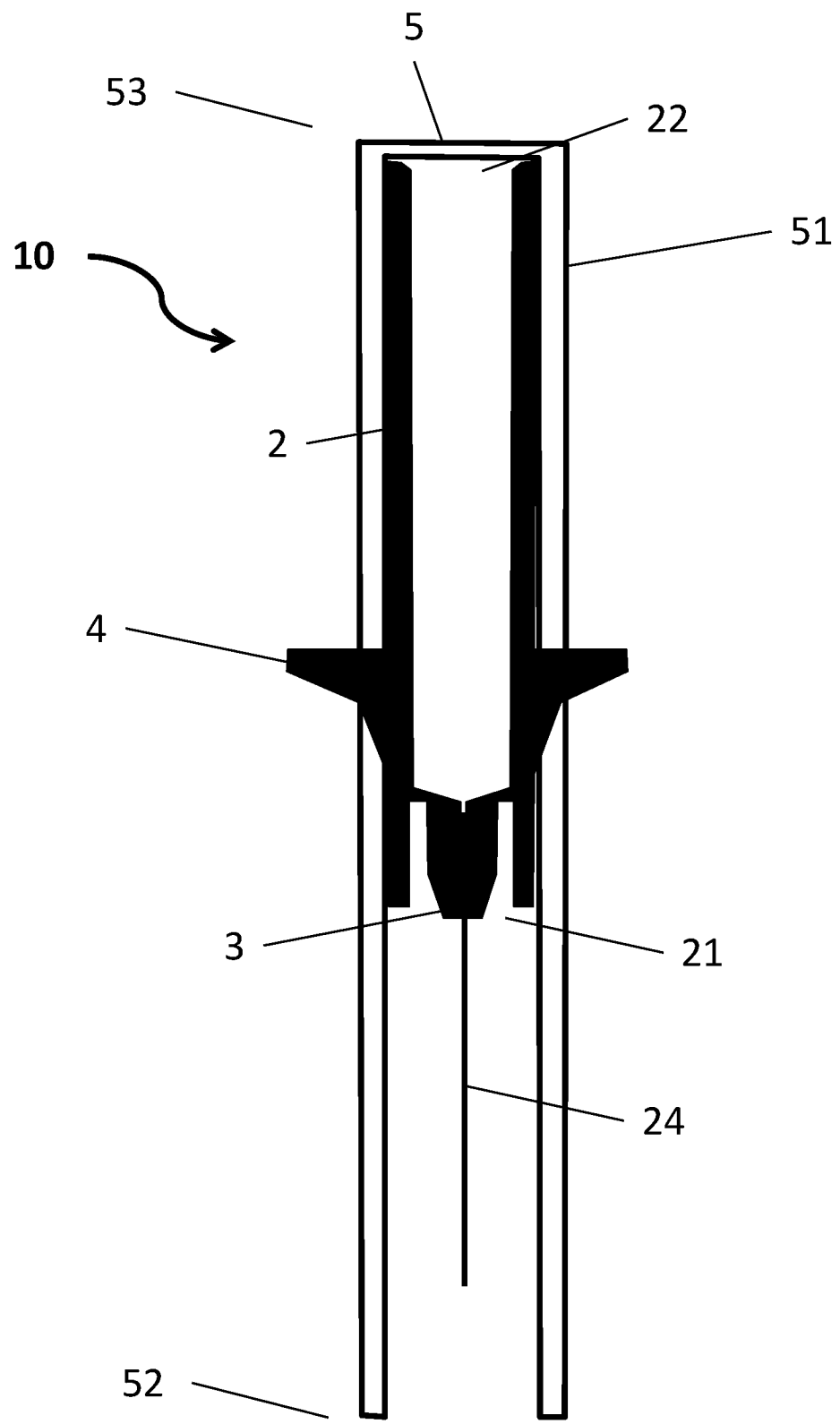
FIG. 4 shows an injector for preventing accidental needle sticks of the invention in a protective position.
Figure 5:
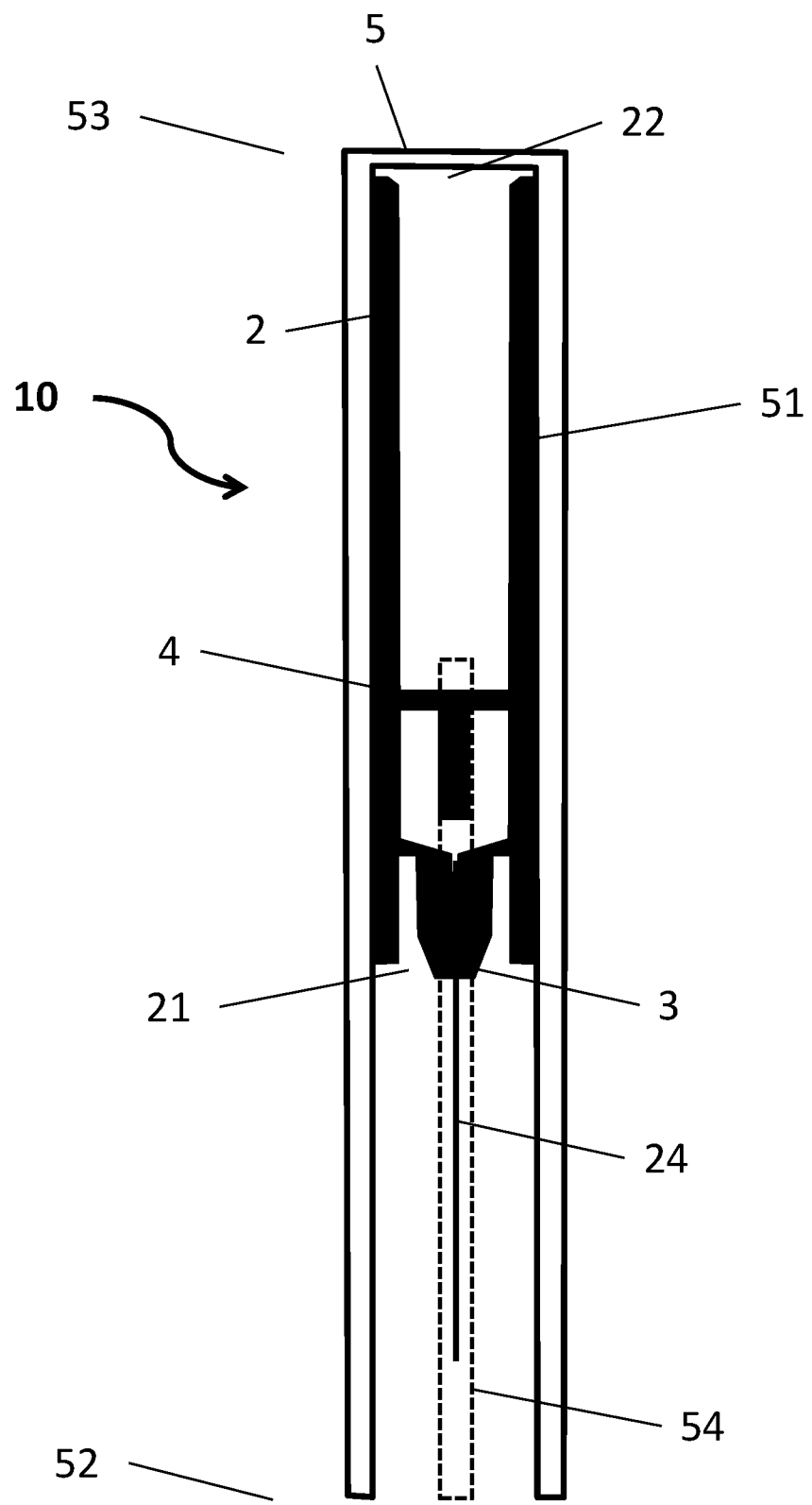
FIG. 5 shows a side view an injector for preventing accidental needle sticks of the invention in a protective position.

FIG. 1 shows an injector 10 for preventing accidental needle sticks. The injector 10 comprises a cylinder 2 extending along a longitudinal axis, an inner wall and an outer wall, the cylinder having an outlet 3 at an outlet end 21 opposite an actuating end 22 and a finger grip 4 on the outer wall, which finger grip is positioned between the outlet end 21 and the actuating end 22. The injector has a piston, which is not shown in FIG. 1. A top view of the injector is shown in FIG. 2. The injector comprises a needle guard 5 for mounting on the outside of the cylinder 2 from the outlet end 21 (as shown in FIG. 1) or the actuating end 22 (as shown in FIG. 4 and FIG. 5), which needle guard 5 comprises a barrel 51 with a mounting end 52 opposite an operating end 53, the barrel 51 having a slot 54, which is not visible in FIG. 1, but which can be seen in the side view shown in FIG. 3, for receiving the finger grip 4 of the cylinder 2 when the needle guard 5 is mounted on the cylinder 2, which slot extends from the mounting 52 end towards the operating end 53. The slot 54 is likewise shown in the side views in FIG. 5 and in the right panel of FIG. 13. When the needle guard 5 is mounted on the cylinder from the actuating end 22 in a protective position, the barrel 51 extends along the longitudinal axis and projects beyond the outlet end 21 of the cylinder 2 so that when a hypodermic needle 24 is attached at the outlet end 21, the barrel 5 protects a user from accidental needle sticks (FIG. 4, FIG. 5). The injector 10 may comprise a hypodermic needle 24, e.g. attached in a way so that its removal requires destruction of the injector, i.e. permanently attached, or the hypodermic needle 24 may be attached in a way allowing removal. In an embodiment the injector 10 does not comprise a hypodermic needle 24 but is designed to be used with standard hypodermic needles of the field.

The cylinder 2 may comprise guide vanes (not shown) at the actuating end 22 of the cylinder for ensuring correct horizontal mounting of the needle guard 5 and showing the finger grip 4 for interaction with the slot 54. The cylinder 2 may further comprise vertical stability fins (not shown) for stable injection and mounting of needle guard before dismantling.

The cylinder 2 may have an outside diameter creating an inward protrusion (not shown), e.g. as a rectangular outward protrusion or a circular protrusion for interaction with outward protrusions of the barrel. The cylinder 2 may have backstop(s) as an outward protrusion of a triangular shape.

Figure 6:
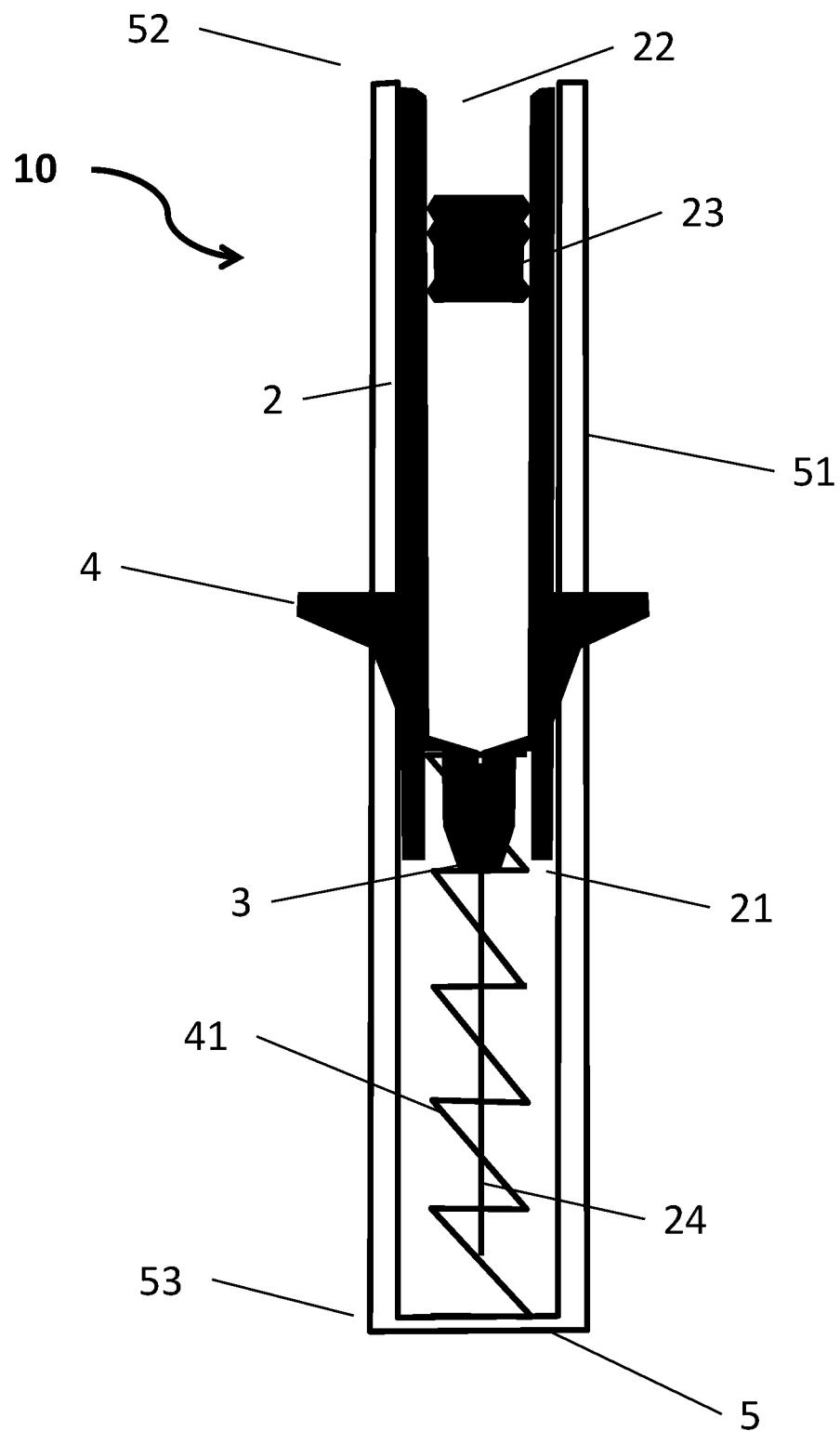
FIG. 6 shows an injector for preventing accidental needle sticks of the invention having a compression spring in a storage position.
Figure 7:
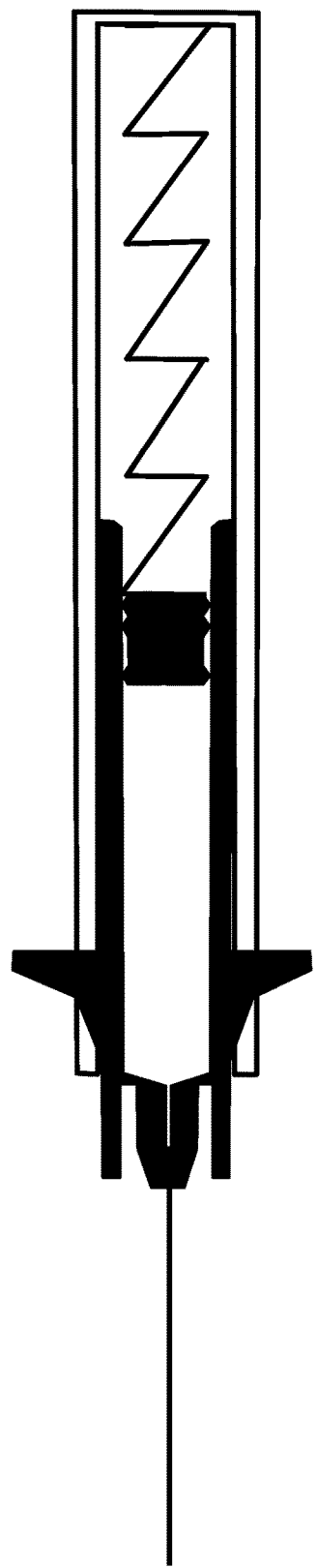
FIG. 7 shows an injector for preventing accidental needle sticks of the invention having a compression spring.
Figure 8:
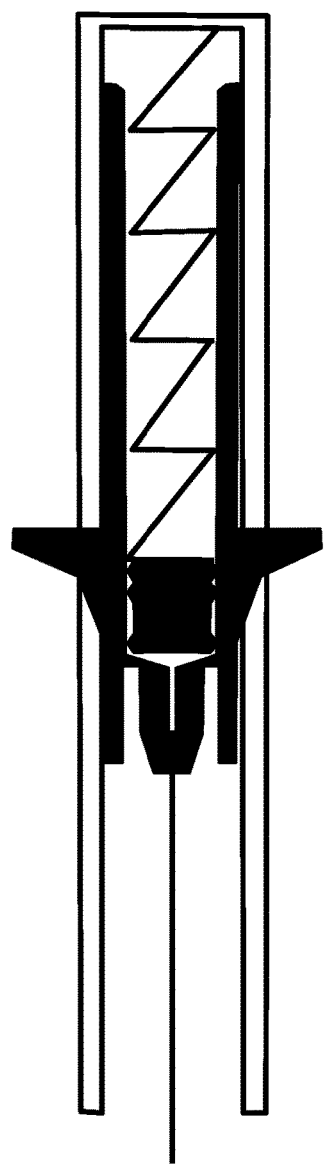
FIG. 8 shows an injector for preventing accidental needle sticks of the invention having a compression spring in a post-injection position.
Figure 9:
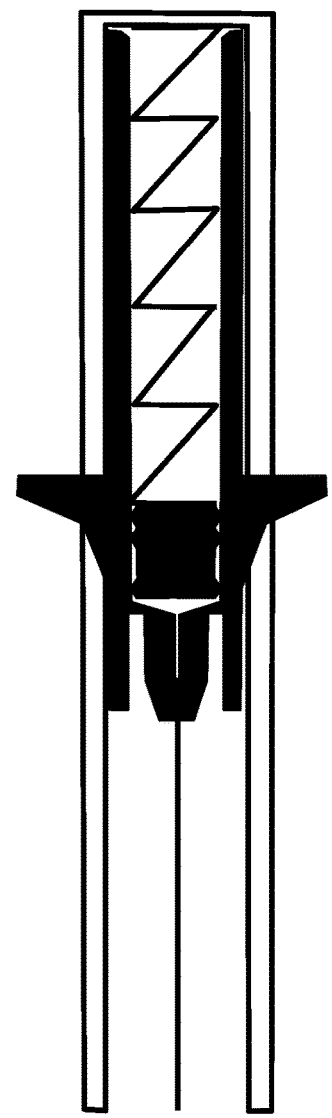
FIG. 9 shows an injector for preventing accidental needle sticks of the invention having a compression spring in a protective position.

The needle guard 5 may be provided with a device for actuating the piston 23, which can move the piston from the actuating end towards the outlet end of the cylinder when the needle guard 5 is mounted on the cylinder 2 from the actuating end 22. FIG. 6 shows an embodiment where the device for actuating the piston 23 is a compression spring 41. The compression spring 41 is attached at the operating end 53 of the needle guard 5, and when the needle guard is mounted in the storage position, as shown in FIG. 6, the compression spring 41 may be slightly compressed. The barrel 51 and the cylinder 2 may be provided with appropriate devices, e.g. barbs or the like (not shown) for retaining the needle guard 5 in the storage position. When the needle guard 5 is removed from the outlet end 21 the compression spring will extend to its relaxed state since no extending force is applied. The needle guard 5 is mounted on the actuating end 22 of the cylinder 2 and the needle guard 5 is pushed toward the outlet end 21 of the cylinder 2, and the compression spring 41 will contact the piston 23 and push the piston 23 toward the outlet end 21 thereby emptying the cylinder 2. The procedure is illustrated in FIG. 7, FIG. 8 and FIG. 9. In FIG. 8 the needle guard 5 is shown in its post-injection position. In FIG. 9 the needle guard 5 is shown in its protective position.

Figure 10:
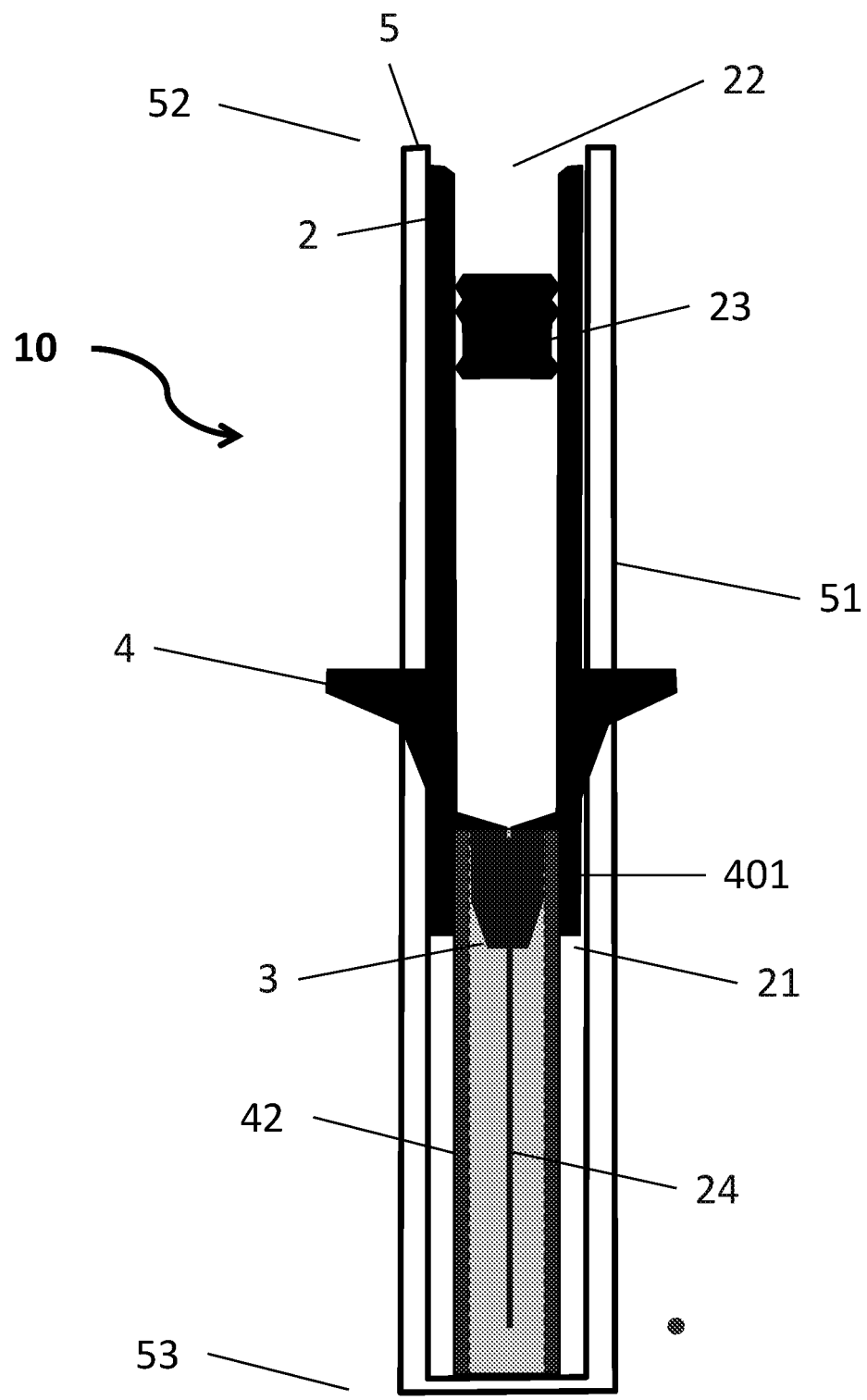
FIG. 10 shows an injector for preventing accidental needle sticks of the invention having a needle cap in a storage position.
Figure 11:
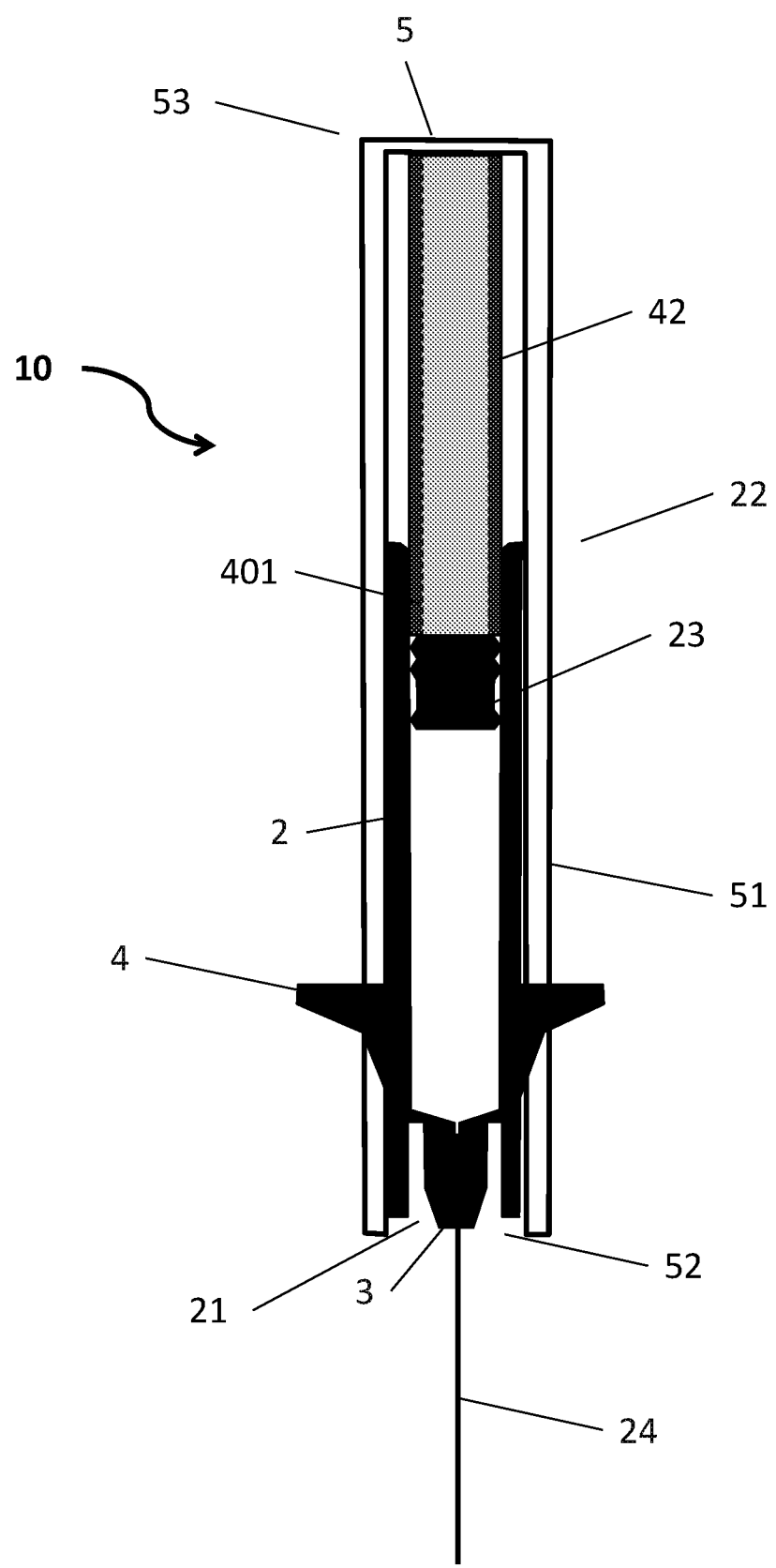
FIG. 11 shows an injector for preventing accidental needle sticks of the invention having a needle cap.
Figure 12:
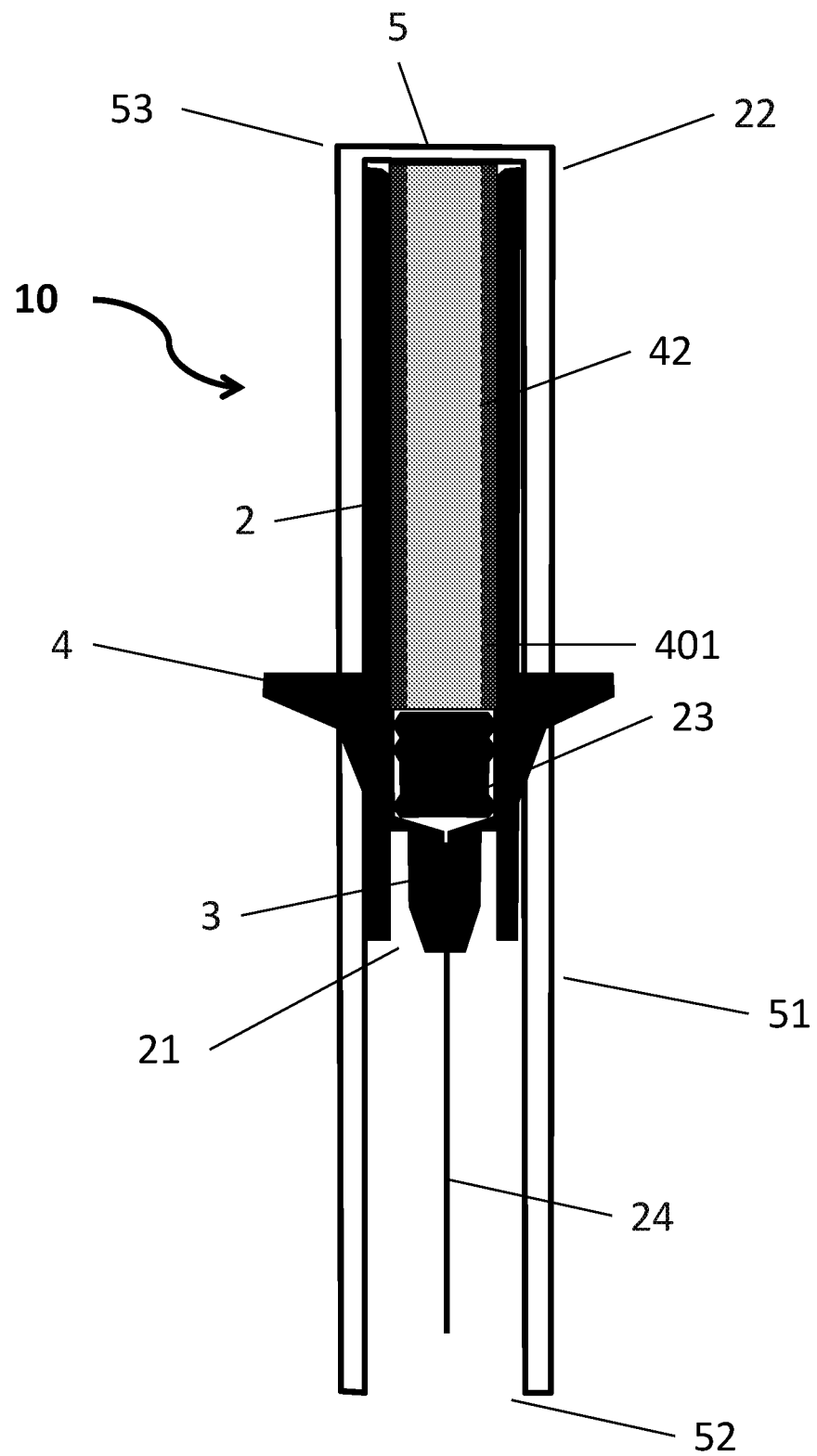
FIG. 12 shows an injector for preventing accidental needle sticks of the invention with a needle cap in its protective position.

In another embodiment, shown in FIG. 10 to FIG. 12, the injector 2 has a needle guard 5 with a device for actuating the piston in the form of a needle cap 42. The needle cap 42 is fastened at the actuating end 53 of the needle guard 5.

In another embodiment, shown in FIG. 13 to FIG. 16, the device for actuating the piston is a needle cap 42 having a tubular section 401 with a fastening end comprising a device 431 in the form of a push plate, e.g. of an thermoplastic elastomer (TPE), for fastening the needle cap to an inside wall of the barrel 51 at a complementary fastening device 432, which needle cap 42 has a length, which is equal to or larger than an operating length of the cylinder 2 defined by the distance from the actuating end 22 of the cylinder 2 to the outlet end 21 of the cylinder 2 minus the dimension of the piston 23 parallel with the longitudinal axis. It is to be understood that when the barrel 51 has an oval transverse cross section the complementary fastening device 432 (presented with dotted lines in the left panel of FIG. 13) is located at or close to points on the narrow axis which allows that it together with the device 431 for fastening the needle cap form a flexible, and thereby releasable, fastening. In the left panel of FIG. 13 the barrel 51 is shown at a right angle to the barrel 51 in the right panel where the slot 54 is visible together with the complementary fastening device 432.

In a specific embodiment the barrel 51 is flexible in a transverse direction, and the needle cap 42 at the fastening end has a fastening device 431 for engaging a complementary fastening device 432 on the inside wall of the barrel 51, which provide the device for fastening the needle cap to the inside wall of the barrel 51, wherein the fastening is releasable. The barrel 51 may have an oval transverse cross section as shown in FIG. 17 where the oval cross-section and the material of the barrel 51 allow that the smallest dimension of the cross-section is pushed outward to release the fastening. In another embodiment the needle cap 42 has a push-plate of a flexible material, e.g. a TPE or another type of elastomer, thereby providing a releasable fastening between the fastening device 431, the push-plate, and the complementary fastening device 432 (see FIG. 15 and FIG. 16).

Figure 13:
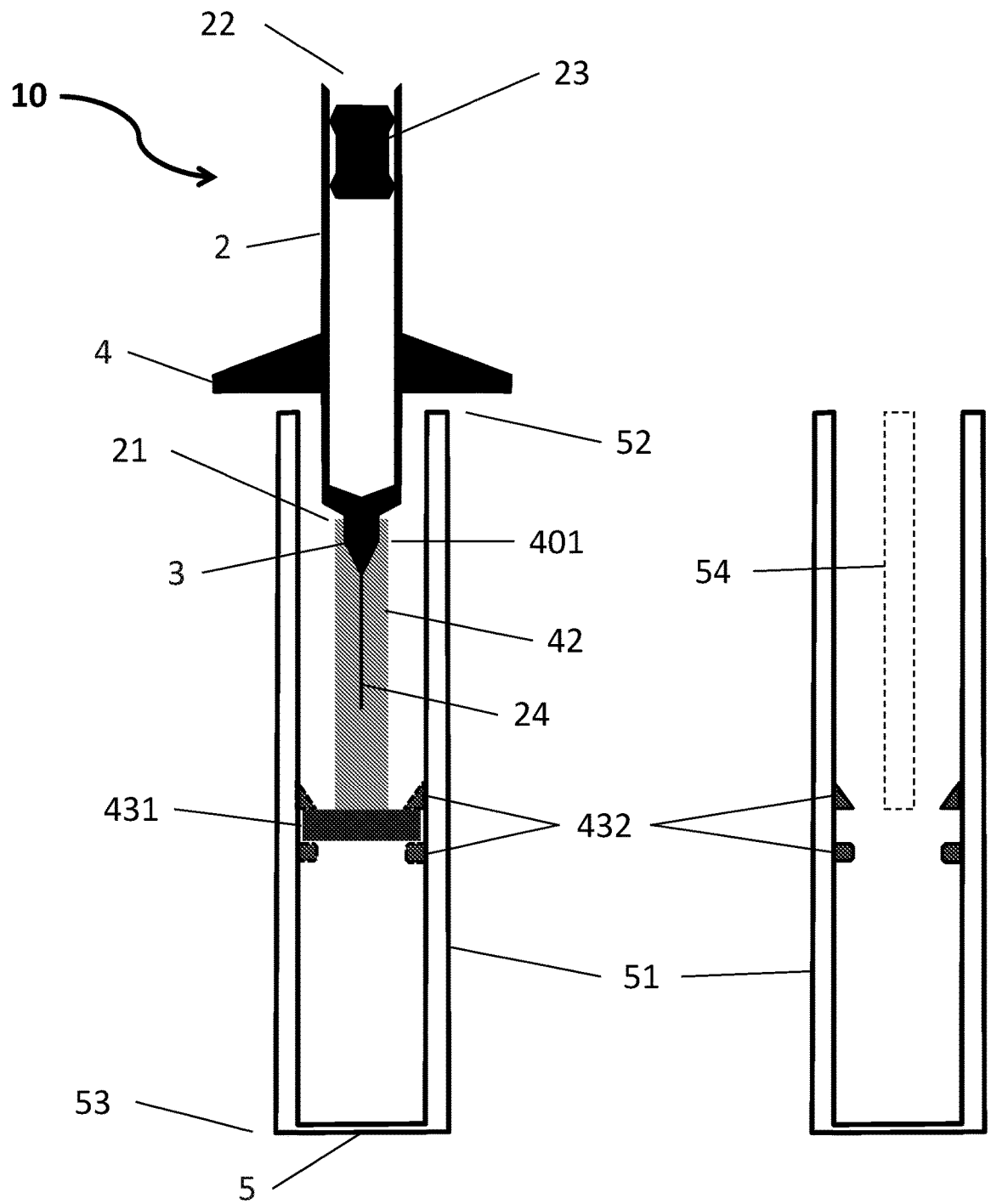
FIG. 13 shows an injector for preventing accidental needle sticks of the invention having a needle cap in a storage position.
Figure 14:
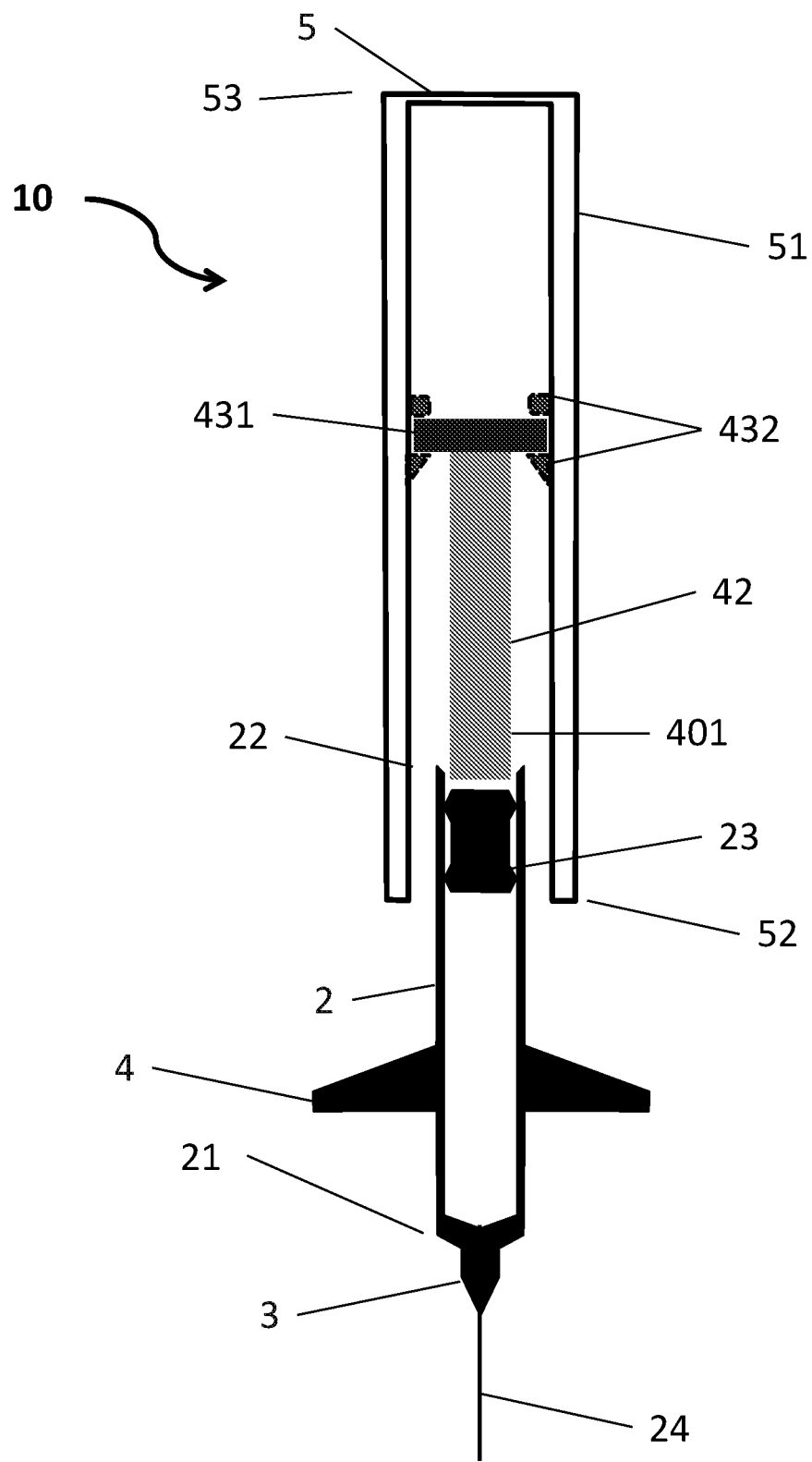
FIG. 14 shows an injector for preventing accidental needle sticks of the invention having a needle cap.
Figure 15:
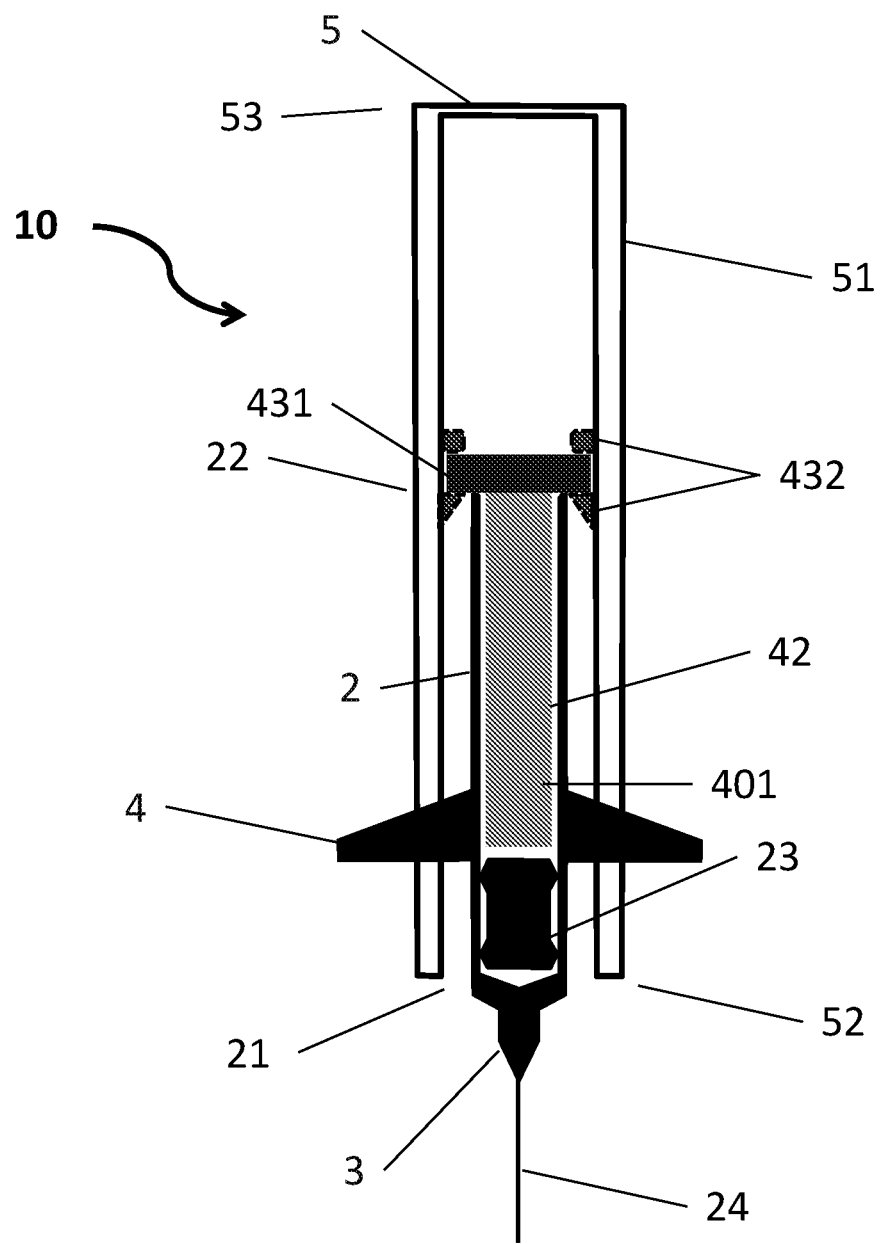
FIG. 15 shows an injector for preventing accidental needle sticks of the invention having a needle cap in a post-injection position.
Figure 16:
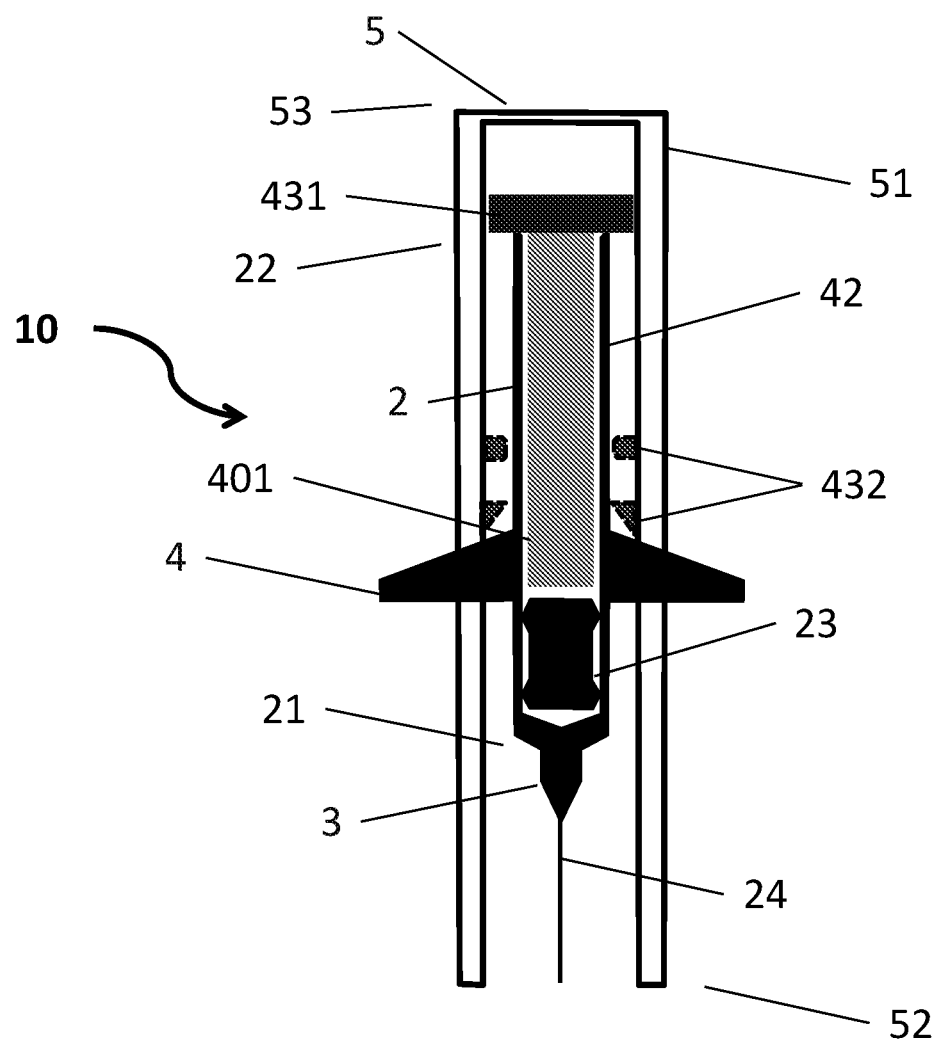
FIG. 16 shows an injector for preventing accidental needle sticks of the invention having a needle cap in its protective position.
Figure 17:
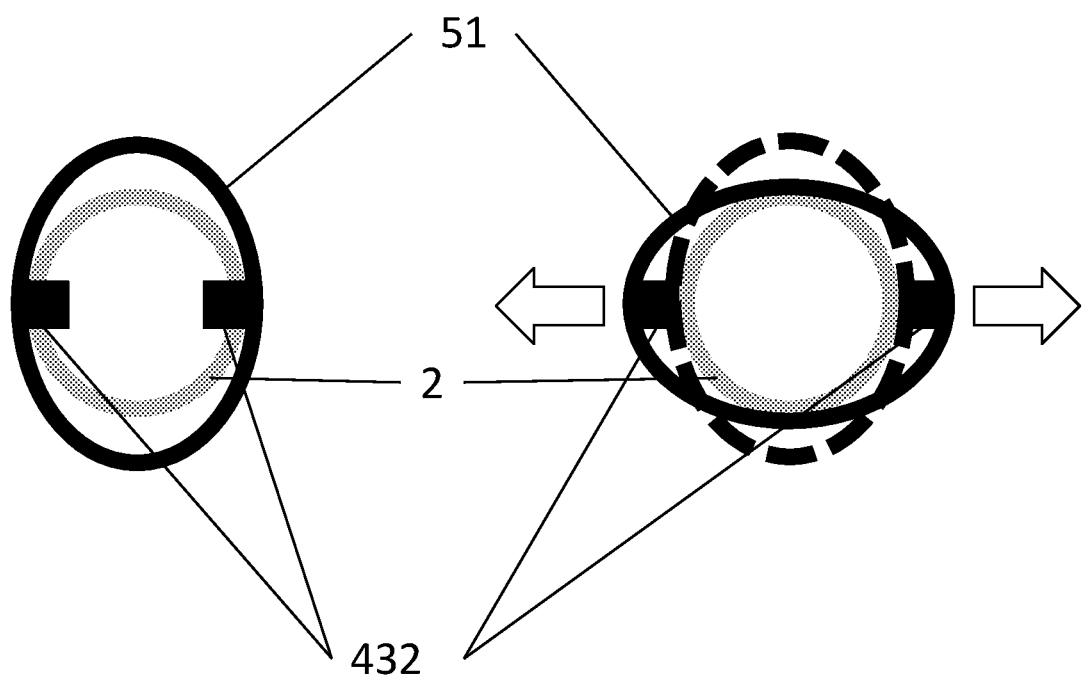
FIG. 17 shows a top view of an embodiment of an injector for preventing accidental needle sticks of the invention.

FIG. 13 shows the needle guard 5 in its storage position, FIG. 15 shows the needle guard 5 in its post-injection position, and FIG. 16 shows the needle guard 5 in its protective position.

Figure 18:
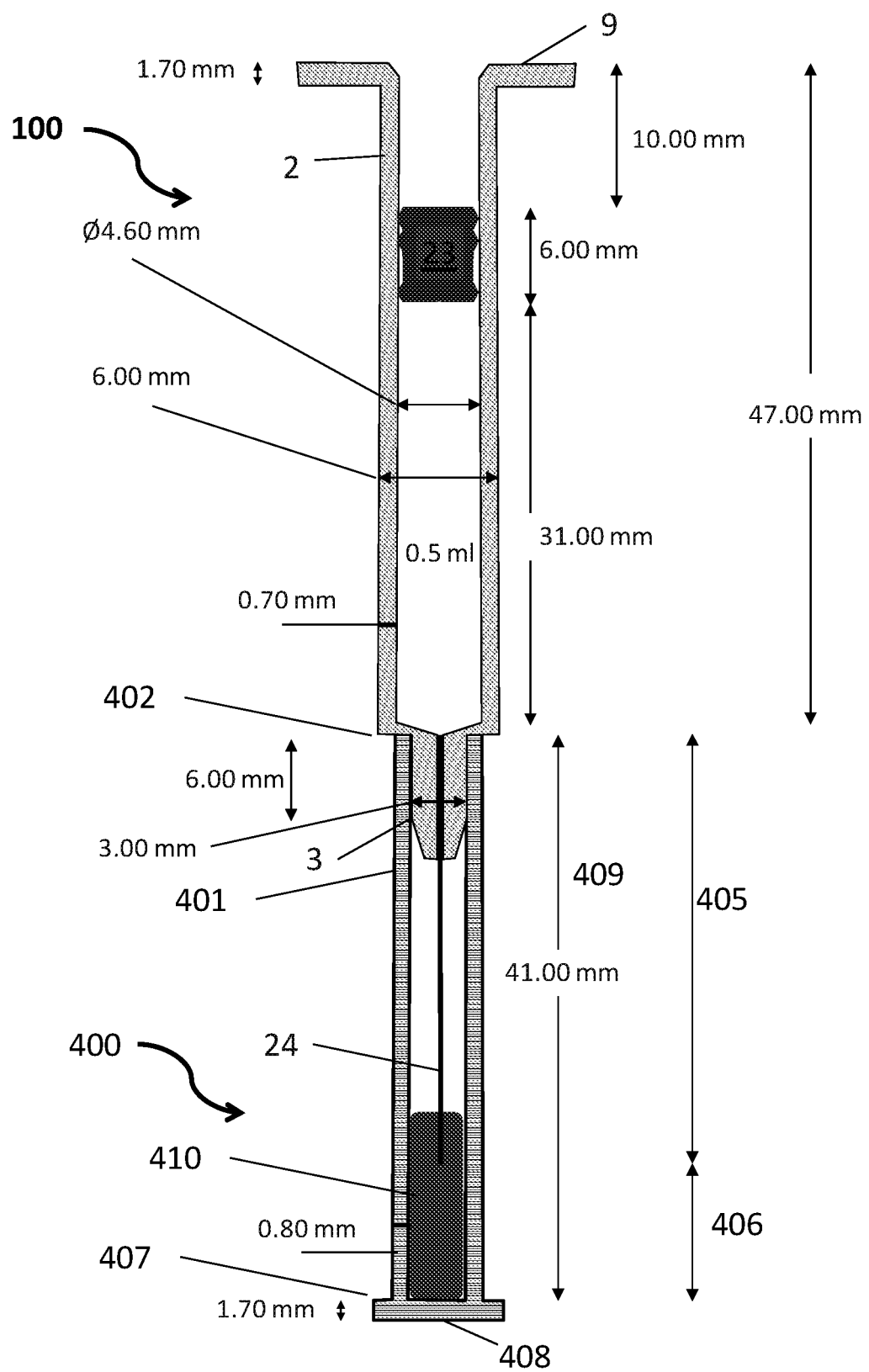
FIG. 18 shows an embodiment of an injector of the invention.
Figure 19:
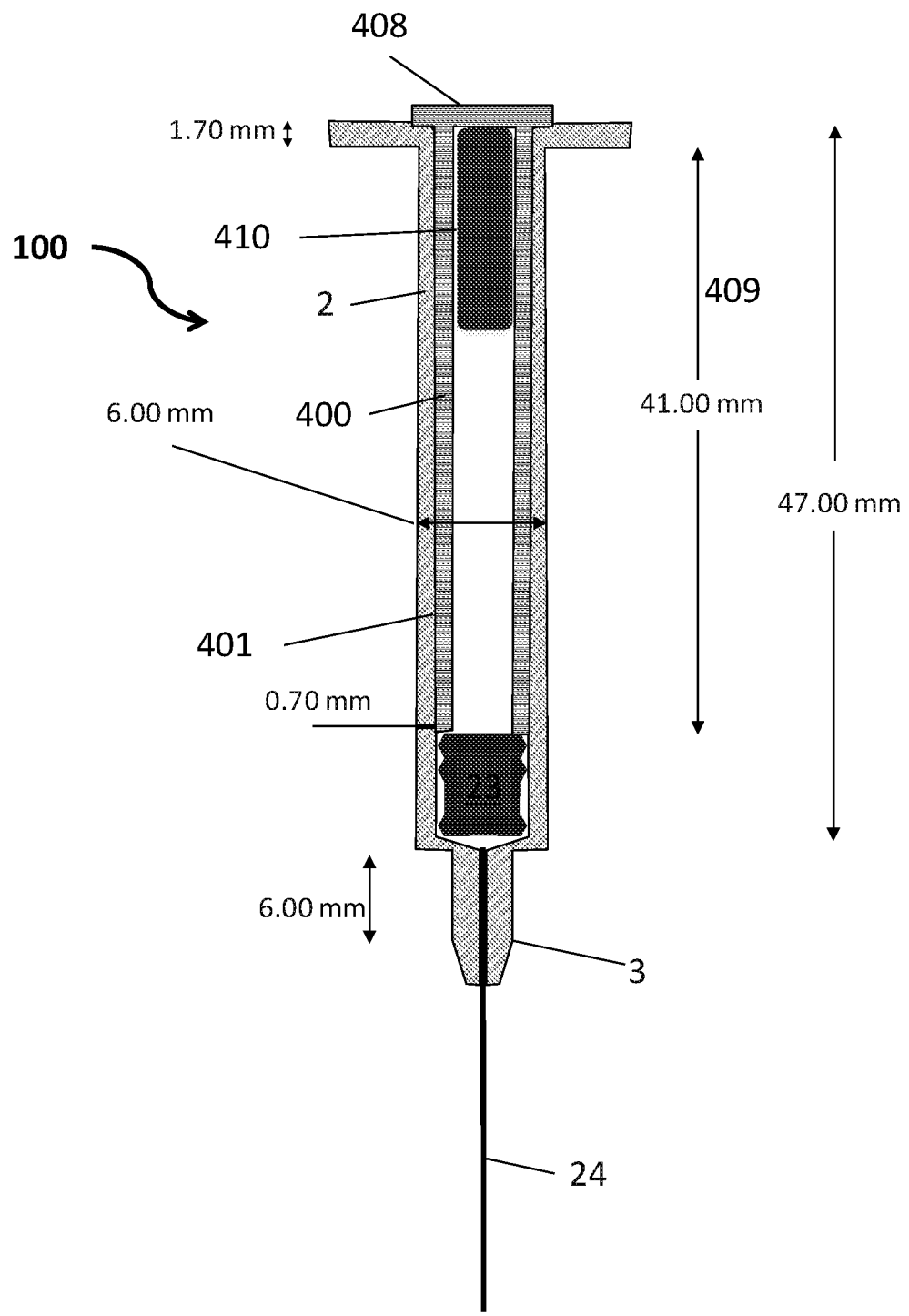
FIG. 19 shows an embodiment of an injector of the invention.

FIG. 18 and FIG. 19 show the second aspect of the invention. Thus, FIG. 18 and FIG. 19 show an injector 100 comprising a cylinder 2 with a longitudinal axis and an inner wall and an outlet 3 at an outlet end 21 of the cylinder 2 opposite an actuating end 22 of the cylinder 2. The injector has a piston 23 having a piston body and a deformable sealing element, which deformable sealing element abuts the inner wall of the cylinder at an abutting interface and seals an annular gap between the piston body and the inner wall of the cylinder 2 when the piston 23 is inserted in the cylinder 2. The injector has a needle cap 400 having a tubular section 401 for actuating the piston 23, which needle cap 400 has a needle insertion end 402 comprising an engagement device for sealingly engaging a complementary engagement device of the outlet 3 of the cylinder 2 when the needle cap 400 is mounted on the cylinder 2, which needle cap 400 has a length 409, which is equal to or larger than an operating length 405 of the cylinder defined by the distance from the actuating end 22 of the cylinder to the outlet end 21 of the cylinder 2 minus the dimension 406 of the piston 23 parallel with the longitudinal axis, which tubular section 401 consists of an elastomeric material. The elastomeric material may a be a TPE, such as a styrene block copolymer (SBC) selected from the list consisting of hydrogenated SBC or non hydrogenated SBS or alloys of these. In a specific embodiment the tubular section 401 has a Shore A hardness in the range of 50 to 90.

The needle cap 400 at a needle protection end 407 opposite the needle insertion end 402 has a push-plate 408 having a larger transverse dimension than a transverse dimension of the needle cap 400. The push plate 408 may be disc shaped, and it may comprise an elastomeric material, e.g. a TPE.

The needle cap 400 may comprise a plug 410, which seals the hypodermic needle 24 when the engagement device is engaging the complementary engagement device of the outlet 3 of the cylinder 2. The plug 410 thus adds a further fail-safe mechanism for sealing the contents of the cylinder 2.

Figure 20:
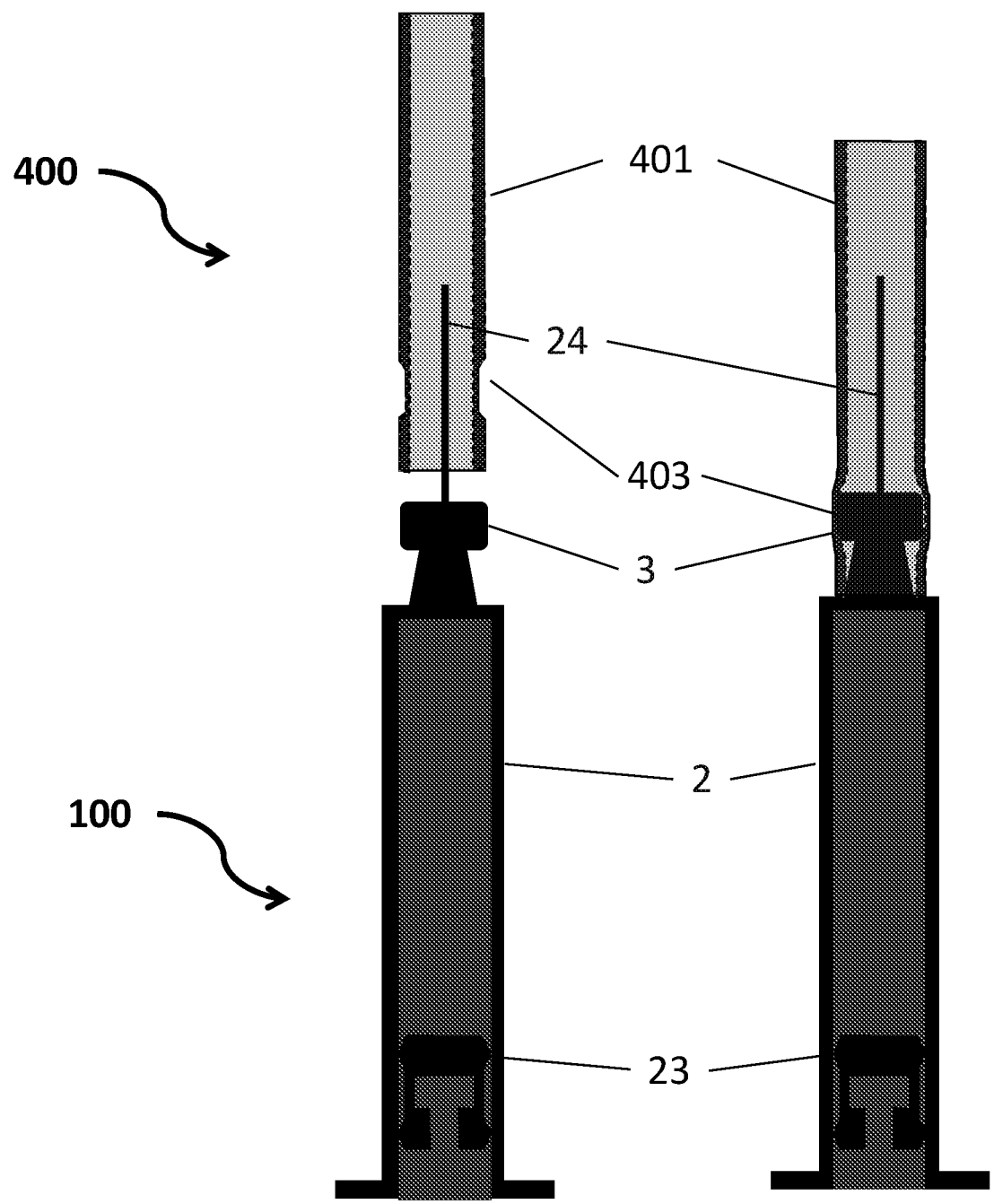
FIG. 20 shows an embodiment of an injector of the invention.

In the embodiment shown in FIG. 20 the needle cap 400 the engagement device 403 comprises a lower material thickness than the material thickness of the tubular section 401. The left panel of FIG. 20 shows the needle cap 400 before mounting on the outlet 3, and the right panel shows the needle cap 400 mounted on the outlet 3. This embodiment is particularly suited for an injector 100 having a glass cylinder 2, where the outlet 3 is typically bigger, due to higher tolerances of manufacturing glass syringes, than for a cylinder of an injection moulded thermoplastic polymer. The material thickness of the engagement device 403 may for example be in the range of 0.2 mm to 1.0 mm. The lower material thickness allows easier mounting of the needle cap 400 on the outlet 3 of the cylinder 2. The same effect can be obtained when the engagement device 403 comprises perforations (not shown). The embodiment in FIG. 20 has a piston 23 with a hollow section for housing, and optionally engaging, a piston rod (not shown).

Figure 21:
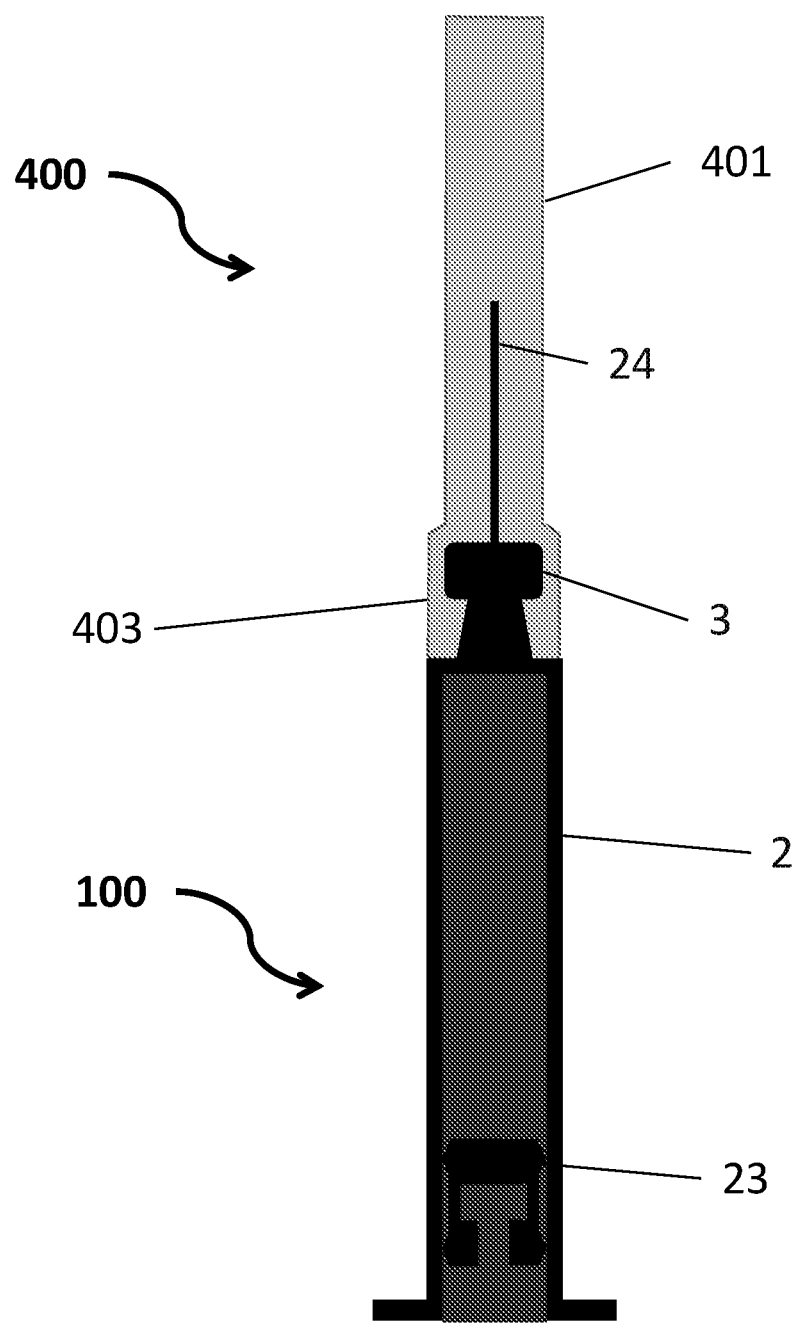
FIG. 21 shows an embodiment of an injector of the invention.

A further embodiment suited for an injector 100 having a glass cylinder 2 is shown in FIG. 21, where an inner cross-sectional area of the engagement device 403 is larger than an inner cross-sectional area of the tubular section 401. This needle cap 400 of this embodiment can likewise be more easily mounted on the outlet 3 of a glass cylinder 2.

Figure 22:
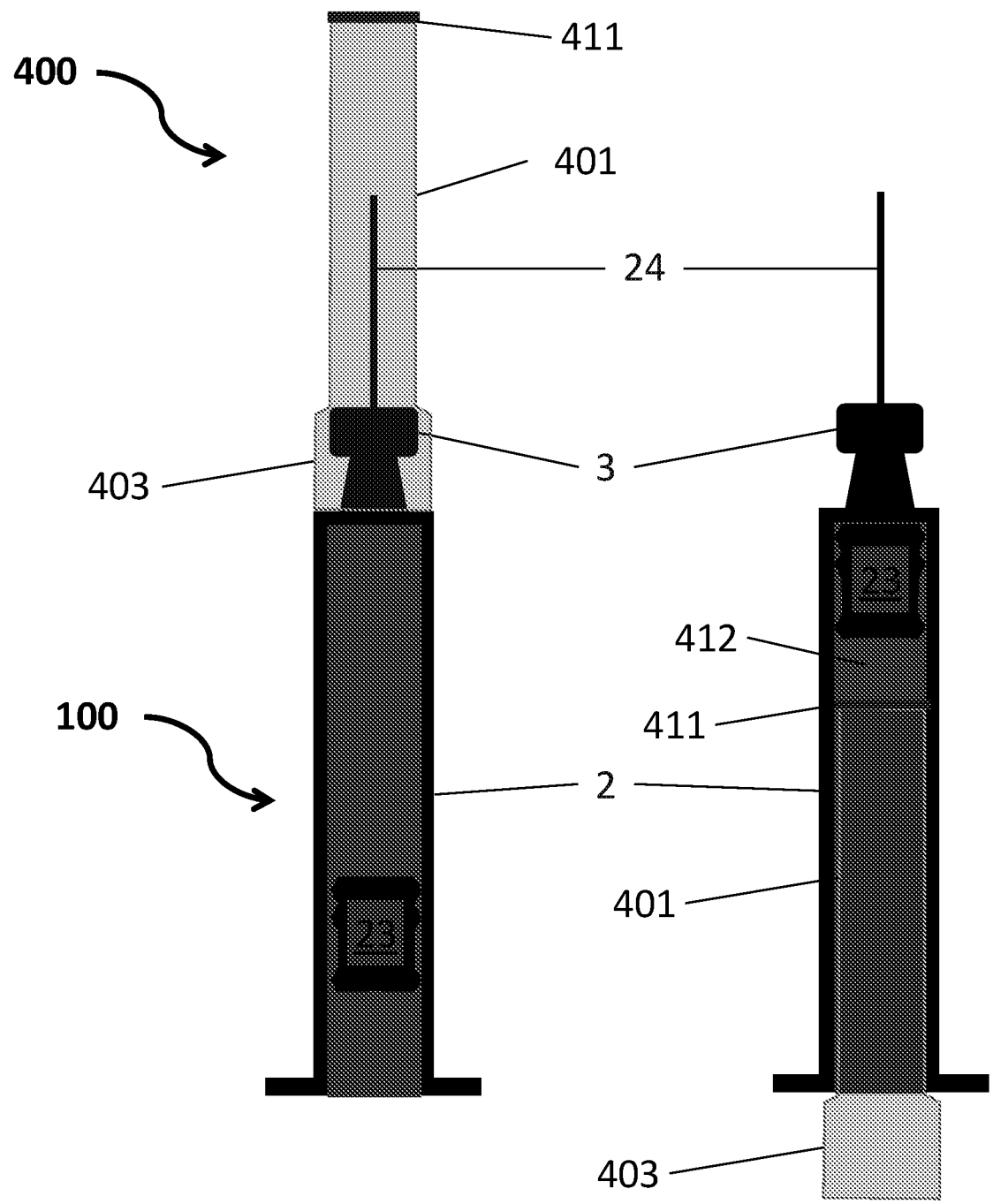
FIG. 22 shows an embodiment of an injector of the invention with an air plug device.

FIG. 22 shows an embodiment of the injector where the tubular section 401 of the needle cap 400 an air plug device 411. In the left panel the needle cap 400 is mounted on the outlet 3 of the cylinder 2, and in the right panel the needle cap has been inserted into the cylinder 2 and the piston 23 has been pushed to the outlet end of the cylinder 2 by the compressed air 412 formed by the air plug device 411.

The invention claimed is:

1. An injector for preventing accidental needle sticks, comprising:
    a cylinder extending along a longitudinal axis, an inner wall and an outer wall, the cylinder having an outlet at an outlet end opposite an actuating end and a finger grip on the outer wall, which finger grip is positioned between the outlet end and the actuating end;
    a piston having a piston body and a deformable sealing element, which deformable sealing element abuts the inner wall of the cylinder at an abutting interface and seals an annular gap between the piston body and the inner wall of the cylinder when the piston is inserted in the cylinder;
    a needle guard for mounting on the outside of the cylinder from the outlet end or the actuating end, which needle guard comprises a barrel with a mounting end opposite an operating end, the barrel having a slot for receiving the finger grip of the cylinder when the needle guard is mounted on the cylinder, which slot extends from the mounting end towards the operating end;
    wherein when the needle guard is mounted on the outside of the cylinder from the outlet end, the finger grip is received in the slot for receiving the finger grip; and
    wherein when the needle guard is mounted on the cylinder from the actuating end in a protective position, the barrel extends along the longitudinal axis and projects beyond the outlet end of the cylinder so that when a hypodermic needle is attached at the outlet end, the barrel protects a user from accidental needle sticks.

2. The injector according to claim 1, further comprising a hypodermic needle.

3. The injector according to claim 1, wherein the needle guard is provided with a device for actuating the piston, which can move the piston from the actuating end towards the outlet end of the cylinder when the needle guard is mounted on the cylinder from the actuating end.

4. The injector according to claim 3, wherein the device for actuating the piston is a compression spring arranged at the operating end of the needle guard.

5. The injector according to claim 4, wherein the compression spring is a helical compression spring.

6. The injector according to claim 4, wherein the compression spring has a compression constant, k, in the range of 0.01 N/mm to 1 N/mm, as determined from the relation: k=F/X, where F is the force applied and X is the displacement of the compression spring.

7. The injector according to claim 3, wherein the device for actuating the piston is a needle cap having a tubular section with a fastening end comprising a device for fastening the needle cap to an inside wall of the barrel, which needle cap has a length, which is equal to or larger than an operating length of the cylinder defined by the distance from the actuating end of the cylinder to the outlet end of the cylinder minus the dimension of the piston parallel with the longitudinal axis.

8. The injector according to claim 7, wherein the barrel is flexible in a transverse direction, and the needle cap at the fastening end has a fastening device for engaging a complementary fastening device on the inside wall of the barrel, which provide the device for fastening the needle cap to the inside wall of the barrel, wherein the fastening is releasable.

9. The injector according to claim 8, wherein the barrel has an oval transverse cross section.

10. The injector according to claim 1, wherein the piston is injection moulded from a TPE.

11. The injector according to claim 10, wherein the piston has a Shore A hardness in the range of 50 to 90.

12. The injector according to claim 10, wherein the injector does not comprise a lubricant.

13. The injector according to claim 10, wherein the cylinder is prefilled with a pharmaceutical composition.

14. The injector according to claim 1, wherein when the needle guard is mounted on the cylinder from the outlet end in a storage position the barrel shields the user of the injector from a hypodermic needle, when a hypodermic needle is attached to the outlet of cylinder.

* * * * *